US006841352B2

(12) United States Patent
Ostanin

(10) Patent No.: US 6,841,352 B2
(45) Date of Patent: Jan. 11, 2005

(54) MATING-BASED METHOD FOR DETECTING PROTEIN—PROTEIN INTERACTION

(75) Inventor: Kirill Ostanin, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 56 days.

(21) Appl. No.: 10/186,386

(22) Filed: Jun. 28, 2002

(65) Prior Publication Data

US 2003/0003439 A1 Jan. 2, 2003

Related U.S. Application Data

(60) Provisional application No. 60/302,535, filed on Jun. 29, 2001.

(51) Int. Cl.$^7$ ............................................. G01N 33/53
(52) U.S. Cl. ................................ 435/7.1; 435/4; 435/6
(58) Field of Search ................................ 435/4, 6, 7.1

(56) References Cited

U.S. PATENT DOCUMENTS

| | | |
|---|---|---|
| 5,283,173 A | 2/1994 | Fields et al. |
| 5,525,490 A | 6/1996 | Erickson et al. |
| 5,585,245 A | 12/1996 | Johnsson et al. |
| 5,637,463 A | 6/1997 | Dalton et al. |
| 5,695,941 A | 12/1997 | Brent et al. |
| 5,733,726 A | 3/1998 | Fu et al. |
| 5,800,998 A | 9/1998 | Glucksmann |
| 5,821,038 A | 10/1998 | Fleer et al. |
| 5,834,247 A | 11/1998 | Comb et al. |
| 5,885,779 A | 3/1999 | Sadowski et al. |
| 5,891,628 A | 4/1999 | Reeders et al. |
| 5,965,368 A | 10/1999 | Vidal et al. |
| 5,981,182 A | 11/1999 | Jacobs, Jr. et al. |
| 6,057,091 A | 5/2000 | Beachy et al. |

OTHER PUBLICATIONS

Strathern et al. Genetics 120: 75–81, 1988.*
Herskowitz, et al., *The Molecular and Cellular Biology of the Yeast Saccharomyces: Gene Expression*, vol. II, Jones et al., Ed., Cold Spring Harbor Laboratory Press, Cold Spring Harbor, New York, 1992.
Chong, Shaorong, et al., "Protein Splicing Involving the Saccharomyces cerevisiae VMA Intein", *The Journal of Biological Chemistry*, Sep. 6, 1996; 271(36):22159–22168.
Wu, Hong, et al., "Protein trans–splicing and functional mini–inteins of a cyanobacterial dnaB intein", *Biochimica et Biophysica Acta*, 1998; 1387:422–432.
Shingledecker, Kaori, et al., "Molecular dissection of the Mycobacterium tuberculosis RecA intein: design of a minimal intein and of a trans–splicing system involving two intein fragments", *Gene*, 1998; 207:187–195.

Karimova, Gouzel, et al., "A Bacterial Two–Hybrid Based on a Reconstituted Signal Transduction Pathway", *Proc. Nat. Acad. Sce.*, May 1998; 95:5752–5756.
Severinov, Konstantin, et al., "Expressed Protein Ligation, a Novel Method for Studying Protein—Protein Interactions in Transcription", *The Journal of Biological Chemistry*, Jun. 26, 1998; 273(26):16205–16209.
Wu, Hong, et al., "Protein trans–splicing by a split intein encoded in a split DnaE gene of Synechocystis sp. PCC6803", *Proc. Natl. Acad. Sci. USA*, Aug. 1998; 95:9226–9231.
Lew, Belinda M., et al., "Characteristics of Protein Splicing in trans Mediated by a Semisynthetic Split Intein", *Biopolymers*, 1999; 51:355–362.
Xu, Rong, et al., "Chemical ligation of folded recombinant proteins: Segmental isotopic labeling of domains for NMR studies", *Proc. Natl. Acad. Sci. USA*, Jan. 1999; 96:388–393.
Evans, Thomas C., Jr., et al., "The in Vitro Ligation of Bacterially Expressed Proteins Using an Intein from *Methanobacterium thermoautotrophicum*", *The Journal of Biological Chemistry*, Feb. 12, 1999; 274(7):3923–3926.
Remy, Ingrid, et al., "Clonal Selection and In Vivo Quantitation of Protein Interactions with Protein–Fragment Completion Assays", *Proc. Natl. Acad. Sci.*, May 1999; 96:5394–5399.
Amitai, Gil, et al., "Fine–tuning an engineered intein", *Nature Biotechnology*, Sep. 1999; 17:854–855.
Evans, Thomas C., Jr., et al., "Protein trans–Splicing and Cyclization by a Naturally Split Intein from the dnaE Gene of *Synechocystis* Species PCC6803", *The Journal of Biological Chemistry*, Mar. 31, 2000; 275(13):9091–9094.
Ozawa, Takeaki, et al., "A Fluorescent Indicator for Detecting Protein—Protein Interactions in Vivo Based on Protein Splicing", *Analytical Chemistry*, Nov. 1, 2000; 72(21):5151–5157.
Ozawa, Takeaki, et al., "Split Luciferase as an Optical Probe for Detecting Protein—Protein Interactions in Mammalian Cells Based on Protein Splicing", *Analytical Chemistry*, Jun. 1, 2001; 73(11):2516–2521.

* cited by examiner

*Primary Examiner*—James Ketter
*Assistant Examiner*—David Lambertson
(74) *Attorney, Agent, or Firm*—Jay Z. Zhang; Herbert L. Ley, III; Myriad IP Dept.

(57) ABSTRACT

The present invention provides a mating-based yeast two-hybrid system for determining whether a test polypeptide interacts with another test polypeptide in the presence or absence of one or more test compounds. The system is useful in detecting protein-protein interactions and in identifying compounds capable of modulating protein-protein interactions.

57 Claims, 18 Drawing Sheets

__MATING-BASED METHOD FOR DETECTING PROTEIN— PROTEIN INTERACTION__

RELATED U.S. APPLICATION

This application claims under 35 U.S.C. §119(e) the benefit of U.S. Provisional Application Ser. No. 60/302,535 filed on Jun. 29, 2001, which is incorporated herein by reference.

FIELD OF THE INVENTION

The present invention generally relates to methods for detecting protein-protein interactions, and particularly to yeast two-hybrid systems for detecting protein-protein interactions.

BACKGROUND OF THE INVENTION

The yeast two-hybrid system has proven to be a powerful method for the discovery of specific protein interactions in vivo. See generally, Bartel and Fields, eds., *The Yeast Two-Hybrid System*, Oxford University Press, New York, N.Y., 1997. The yeast two-hybrid technique is based on the fact that the DNA-binding domain and the transcriptional activation domain of a transcriptional activator contained in different fusion proteins can still activate gene transcription when they are brought into proximity to each other. In a yeast two-hybrid system, two fusion proteins are expressed in a yeast cell. One has a DNA-binding domain of a transcriptional activator fused to a test protein. The other, on the other hand, includes a transcriptional activating domain of the transcriptional activator fused to another test protein. If the two test proteins interact with each other in vivo, the two domains of the transcriptional activator are brought together reconstituting the transcriptional activator and activating a reporter gene controlled by the transcriptional activator. See FIG. 1. See also, e.g., U.S. Pat. No. 5,283,173.

Because of its simplicity, efficiency and reliability, the yeast two-hybrid system has gained tremendous popularity in many areas of research and development. Yeast cells are eukaryotic cells. The interactions between mammalian proteins detected in the yeast two-hybrid system typically are bona fide interactions that occur in mammalian cells under physiological conditions. As a matter of fact, numerous mammalian protein-protein interactions have been identified using the yeast two-hybrid system. The identification of such protein-protein interactions has contributed significantly to the understanding of many biological processes.

In addition, the yeast two-hybrid system can also be used in drug screening to identify compounds capable of modulating a particular protein-protein interaction. Indeed, a modified version of the yeast two-hybrid system, the so called "reverse two-hybrid assay," is one of the most powerful assays for identifying chemical inhibitors of protein-protein interactions. In essence, a reverse yeast two-hybrid assay employs one or more counterselectable reporters such that yeast cells harboring such reporters can be positively selected only when a target protein-protein interaction is disrupted by a test compound. Various reverse two-hybrid systems are disclosed in, e.g., U.S. Pat. Nos. 5,525,490; 5,733,726; 5,885,779; and 5,965,368.

However, these reverse two-hybrid methods have serious drawbacks. For example, the counter-selectable signals caused by a test compound typically are reversible. Consequently, continued dissociation of target proteins is often required during an assay in order to provide an adequate selection signal. However, continued dissociation of target proteins during an assay is typically difficult, if not impossible, to achieve. The test compounds that dissociate target proteins may not be stable and can decompose during the assay. Prolonged exposure of test compounds to host yeast cells may lead to activation of the host cellular machineries to metabolize or eject the compounds. Some test compounds may only be effective at certain phases of host cell growth and become ineffective as the host cell grows. Another factor that exacerbates the problems is that the effective concentration of a test compound is typically unknown a priori and can be within a rather narrow range. In light of these constraints, a range of concentrations must be examined under conditions where the concentrations are stable. Such exhaustive testing is antithetical to high-throughput screening. Instead, a single concentration is often selected for testing in liquid assays, notwithstanding the possibility that the effective concentration may be significantly different from the tested concentration. Alternatively, solid agar assays can be used, in which a concentrated solution of a test compound is spotted onto a lawn of cells and diffusion establishes a dynamic concentration gradient. Still, given the instability of the concentration gradient, compounds that are active over a narrow concentration range may escape identification.

Therefore, there is a great need for two-hybrid systems that can be used in large-scale high throughput screening assays without the above shortcomings.

SUMMARY OF THE INVENTION

The present invention provides a novel mating-based yeast two-hybrid system for determining whether one test polypeptide interacts with another test polypeptide in the presence or absence of one or more test compounds. Specifically, the system of the present invention exploits the well-characterized yeast genetic mechanism that controls mating between yeast haploid alpha- and a-cells. In the system, two fusion proteins are recombinantly expressed in a yeast haploid cell. One fusion protein contains one test polypeptide fused to an effector polypeptide, while the other fusion protein contains the other test polypeptide fused to another effector polypeptide. The yeast haploid cell is provided such that the expression of a-specific genes or alpha-specific genes in the haploid cell is regulated by an interaction between the two test polypeptides in the two fusion proteins, whereby the yeast haploid cell is either sterile or capable of mating depending upon the presence or absence of a protein-protein interaction between the two test polypeptides in the fusion proteins. Thus, by determining whether the yeast haploid cell is capable of mating to form a yeast diploid cell in the presence or absence of one or more test compounds, the presence or absence of an interaction between the two test polypeptides can be determined.

As will be apparent from the detailed disclosure below, in the mating-based yeast two-hybrid system of the present invention, an interaction between two test polypeptides or disruption of the interaction can lead to the expression of a particular mating type in a haploid cell. Thus, the haploid cell can be mated with another yeast haploid cell that exhibits an appropriate mating type. Once mating occurs, the two yeast haploid cells form a diploid cell. Since mating is an irreversible event, an interaction between two test polypeptides or disruption of the interaction is accurately reflected and permanently "recorded" in the diploid cells resulted from mating. Thus, the two-hybrid system of the present invention exhibits high sensitivity and is particularly useful in detecting weak or transient protein-protein interactions in screens designed to select compounds capable of disrupting a protein-protein interaction.

For example, when the system of the present invention is used in a reverse two-hybrid screen assay, disruption of an interaction between two proteins can be indicated by a stable readout (diploid cells resulting from mating) that persists independently of continued dissociation or resumed interaction of the proteins. Thus, if a particular concentration of a compound can effectively dissociate two proteins, the present invention can detect that dissociation even when the effective concentration is short-lived or the dissociation is reversible or transient.

Accordingly, in a first aspect, the present invention provides a method for selecting a compound capable of disrupting an interaction between a first test polypeptide and a second test polypeptide which comprises providing a test yeast haploid cell expressing two fusion proteins. One fusion protein contains the first test polypeptide and an effector polypeptide while the other fusion protein contains the second test polypeptide and another effector polypeptide. The test yeast haploid cell is engineered such that it is sterile in the presence of the interaction between the first and second test polypeptides, and exhibits the a- or alpha-mating type when the interaction between the first and second test polypeptides is disrupted. Conveniently, the test yeast haploid cell is co-cultured, in the presence of one or more test compounds, with a reporter yeast haploid cell that has a mating type opposite to the expected mating type of the test yeast haploid cell. The occurrence of mating would indicate that the compounds are capable of disrupting the protein-protein interaction between two test polypeptides. The selected compounds may be useful as drug leads or candidates for treating diseases or disorders involving the protein-protein interaction.

For example, the test yeast haploid cell can be a yeast haploid cell that lacks a functional MAT-alpha1p protein and whose production of a functional MAT-alpha2p protein is controlled by the interaction between the first and second test polypeptides. In another example, the test yeast haploid cell expresses a functional MAT-alpha2p protein, and the production of a functional MAT-alpha1p protein in the cell is controlled by an interaction between the first and second test polypeptides.

In a specific embodiment of the selection method of the present invention, a test yeast haploid cell is provided which lacks a functional MAT-alpha1p protein. This can be achieved in a yeast haploid cell by knocking out its MAT-alpha1 gene or introducing deleterious mutations into the MAT-alpha1 gene. The test yeast haploid cell expresses a first fusion protein containing the first test polypeptide fused to a DNA binding domain and a second fusion protein containing the second test polypeptide fused to a transcriptional activation domain. In addition, in the test yeast haploid cell, the MAT-alpha2 gene expression is placed under the control of the interaction between the first and second test polypeptides. For example, MAT-alpha2 protein may be encoded by a reporter gene that contains an operator capable of binding to the DNA binding domain in the first fusion protein. Thus, when the first and second test polypeptides interact with each other, MAT-alpha2 protein is expressed and the test yeast haploid cell is sterile. In contrast, when the protein-protein interaction between the first and second test polypeptides is disrupted, the MAT-alpha2 gene is not expressed and the test yeast haploid cell exhibits the a-mating type. The test yeast haploid cell can be co-cultured with another yeast haploid cell of alpha-mating type in the presence of a compound and under conditions conducive to mating and under conditions to allow only the growth of yeast diploid cells. The formation of yeast colonies would indicate that the compound is capable of disrupting the protein-protein interaction between the first and second test polypeptides.

In another aspect of the present invention, a method for detecting protein-protein interactions is provided. The method can be used for determining whether two proteins interact with each other or for identifying unknown interactors of a particular protein. Essentially, a test yeast haploid cell is provided which expresses two fusion proteins, one containing a first test polypeptide and a first effector polypeptide and the other containing a second test polypeptide and a second effector polypeptide. The haploid cell is engineered such that its sterility and mating type is determined by the synergistic actions of the two effector polypeptides, which are in turn controlled by the interaction between the two test polypeptides. Preferably, the haploid cell is sterile in the absence of an interaction between the two test polypeptides, but exhibits the a- or alpha-mating type when the first test polypeptide interacts with the second test polypeptide. Thus, by detecting whether the yeast haploid cell is capable of mating, the presence or absence of an interaction between the first and second test polypeptides can be determined.

In one embodiment, the test yeast haploid cell expresses a functional MAT-alpha2p protein. The cell lacks a functional MAT-alpha1p protein in the absence of an interaction between the first and second test polypeptides, but produces a functional MAT-alpha1p protein in the presence of an interaction between the first and second test polypeptides. In another embodiment, the test yeast haploid cell lacks a functional MAT-alpha1p protein. It produces a functional MAT-alpha2p protein in the absence of an interaction between the first and second test polypeptides, but lacks a functional MAT-alpha2p protein in the presence of an interaction between the two test polypeptides.

In a specific preferred embodiment, the protein-protein interaction detecting method comprises providing a test yeast haploid cell which lacks a functional MAT-alpha1p protein. The test yeast haploid cell expresses two fusion proteins, one containing a first test polypeptide and a DNA binding domain while the other containing a second test polypeptide and a transcriptional repressor domain. In addition, the test haploid cell further contains a reporter gene encoding MAT-alpha2p protein and comprising an operator capable of binding to the DNA binding domain. When the two test polypeptides do not interact with each other, the reporter gene is expressed and MAT-alpha2p is produced. As a result, the test haploid cell is sterile. On the other hand, in the presence of an interaction between the two test polypeptides, the expression of the MAT-alpha2p is suppressed and the test haploid cell exhibits the a-mating type. Thus, a mating event between the test haploid cell with a reporter yeast haploid cell of alpha-mating type would indicate the interaction between the two test polypeptides.

The present invention also provides a test yeast haploid cell suitable for the methods of the present invention. Specifically, the test yeast haploid cell contains two chimeric genes. One chimeric gene encodes a fusion protein that contains a first test polypeptide and a first effector polypeptide. The other chimeric gene encodes another fusion protein that contains a second test polypeptide and a second effector polypeptide. The two effector polypeptides do not have substantial affinity to each other. However, when brought into proximity with each other, they can initiate or suppress the production of a functional MAT-alpha1p and/or MATalpha2p protein in the yeast haploid cell. In addition, the yeast haploid cell is provided such that it is either sterile or capable of mating depending upon whether or not the two test polypeptides interact with each other to bring the two effector polypeptides into proximity.

In one embodiment of the test yeast haploid cell of the present invention, one of the first and second effector polypeptides is a DNA binding domain and the other is a transcriptional activation domain or transcriptional repressor domain. In addition, the haploid cell contains a reporter gene encoding the MAT-alpha1p or MAT-alpha2p protein whose transcription is controlled by the interaction between the first and second test polypeptides which reconstitutes a quasi-transcriptional activator from the DNA binding domain and the transcriptional activation domain, or a quasi-transcriptional repressor from the DNA binding domain and the transcriptional repressor domain.

In another embodiment, one of the first and second effector polypeptides is a DNA binding domain and the other is a transcriptional activation domain or transcriptional repressor domain. The test yeast haploid cell contains a relay gene encoding a transcriptional activator or repressor capable of activating or suppressing the expression of a reporter gene encoding the MAT-alpha1p or MAT-alpha2p protein. The transcription of the relay gene is controlled by the interaction between the first and second test polypeptides which reconstitutes a quasi-transcriptional activator from the DNA binding domain and the transcriptional activation domain, or a quasi-transcriptional repressor from the DNA binding domain and the transcriptional repressor domain.

In a preferred embodiment, the test yeast haploid cell of the present invention lacks a functional MAT-alpha1p protein. In addition, the test yeast haploid cell contains two chimeric genes encoding two fusion proteins. One fusion protein contains a test polypeptide and a DNA binding domain, and the other fusion protein is composed of another test polypeptide and a transcriptional activation domain. The cell further contains a reporter gene encoding MAT-alpha2p protein and having an operator capable of binding to the DNA binding domain. As a result, the reporter gene is expressed and the yeast haploid cell is sterile in the presence of an interaction between the two test polypeptides. In contrast, the reporter gene is not expressed and the yeast haploid cell exhibits the a-mating type when the protein-protein interaction between said first and second test polypeptides is disrupted.

The present invention also provides a test yeast haploid cell which is incapable of expressing a functional MAT-alpha1p protein. In addition, the production of MAT-alpha2p protein is under the control of an inducible promoter, e.g., the Gal1 promoter. The present invention further provides a test yeast haploid cell which is incapable of expressing a functional MAT-alpha1p protein and whose production of MAT-alpha2p protein is under the control of an operator having a repressor-responsive element.

In yet another aspect of the present invention, a kit is provided for using the methods of the invention in detecting protein-protein interactions or selecting compounds capable of disrupting protein-protein interactions. The kit may contain a test yeast haploid cell of the present invention. Alternatively, the kit may include a test yeast haploid precursor cell that can be used in making a test yeast haploid cell. The kit may further contain a reporter yeast haploid cell of a-mating type, and/or a reporter yeast haploid cell of alpha-mating type.

Thus, in one embodiment, the kit comprises in a compartmentalized carrier, a first yeast haploid cell having a genotype of mat-alpha1$^-$, and a reporter yeast haploid cell of alpha-mating type, wherein the first yeast cell has a first reporting marker and the second yeast cell has a second reporting marker that is different from said first reporting marker. Preferably, the first yeast haploid cell contains a reporter gene encoding a functional MAT-alpha2p protein and having a promoter responsive to a transcriptional activator or repressor not expressed by said first yeast haploid cell.

In another embodiment, the kit comprises, in a compartmentalized carrier, (1) a yeast haploid cell having the genotype of mat-alpha1$^-$, (2) a first expression vector containing a first expression cassette which comprises a first DNA sequence encoding a DNA binding domain operably linked to a first multiple cloning site (MCS), and (3) a second expression vector containing a second expression cassette which comprises a second DNA sequence encoding a transcriptional activation domain or a transcriptional repressor domain, said second DNA sequence being operably linked to a second multiple cloning site (MCS). Preferably, the yeast haploid cell comprises a reporter gene encoding a functional MAT-alpha2p protein and having a promoter capable of binding the DNA binding domain expressed from the first expression vector.

In yet another embodiment, the kit includes two expression vectors. One expression vector contains an expression cassette which comprises, operably linked together, (1) a DNA sequence encoding an N-intein, (2) a multiple cloning site (MCS), and (3) a DNA sequence encoding an N-terminal portion of a transcriptional activator or repressor. Another expression vector contains a second expression cassette which comprises, operably linked together, (1) a DNA sequence encoding a C-intein, (2) a multiple cloning site (MCS), and (3) a C-terminal portion of said transcriptional activator or repressor. The different elements in the two expression cassettes can be arranged such that DNA fragments encoding two test polypeptides can be subcloned in frame into the two multiple cloning sites, respectively, and two fusion proteins can be expressed from the two expression cassettes. Each test polypeptide is expressed as part of one of the two fusion proteins along with the intein elements and portions of the transcriptional activator or repressor. The two fusion proteins are such that in the presence of an interaction between the two test polypeptides, intein-mediated protein splicing takes place and a functional transcriptional activator or repressor is generated. Preferably the kit also includes a yeast haploid cell containing a reporter gene encoding a functional MAT-alpha2p protein or MAT-alpha1p protein. The expression of the reporter gene is controlled by the transcriptional activator or repressor.

In yet another embodiment, the kit of the present invention comprises two expression vectors. One contains an expression cassette which comprises, operably linked together, (1) a first DNA sequence encoding an N-intein, (2) a first multiple cloning site (MCS), and (3) a second DNA sequence encoding an N-terminal portion of MAT-alpha1p or MAT-alpha2p protein. Another expression vector contains another expression cassette which comprises, operably linked together, (1) a third DNA sequence encoding a C-intein, (2) a second multiple cloning site (MCS), and (3) a C-terminal portion of said MAT-alpha1p or MAT-alpha2p protein.

The foregoing and other advantages and features of the invention, and the manner in which the same are accomplished, will become more readily apparent upon consideration of the following detailed description of the invention taken in conjunction with the accompanying examples and drawings, which illustrate preferred or exemplary embodiments.

DETAILED DESCRIPTION OF THE INVENTION

Figure 1:
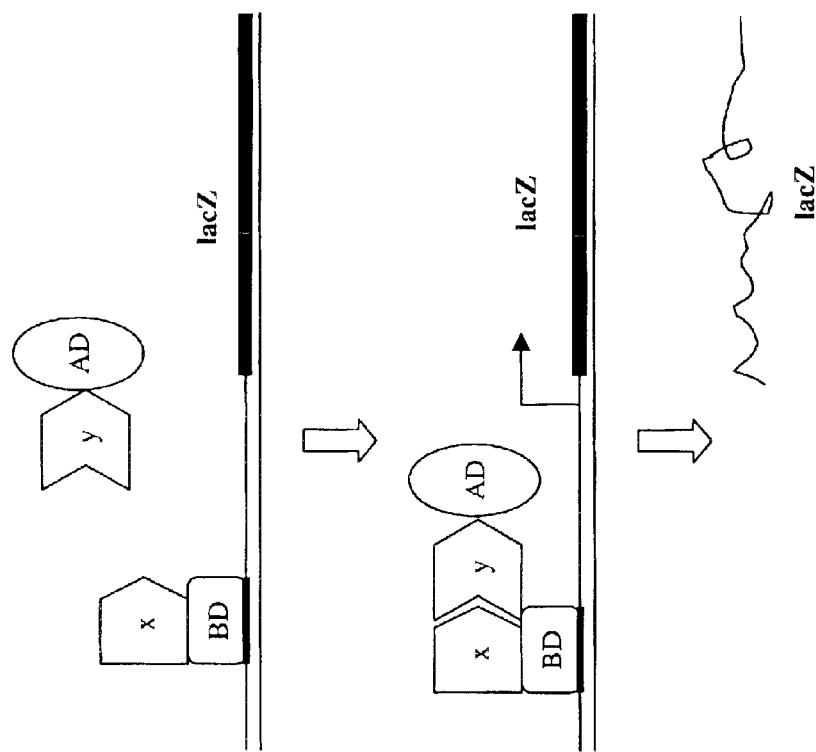
FIG. 1 is an illustration of the classic yeast two-hybrid system known in the art.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

As used herein, the term "interacting" or "interaction" means that two protein fragments, domains or complete proteins exhibit sufficient physical affinity to each other so as to bring the two "interacting" protein domains or proteins physically close to each other. An extreme case of interaction is the formation of a chemical bond that results in continual and stable proximity of the two domains or proteins. Interactions that are based solely on physical affinities, although usually more dynamic than chemically bonded interactions, can be equally effective in co-localizing two proteins. Examples of physical affinities and chemical bonds include but are not limited to, forces caused by electrical charge differences, hydrophobicity, hydrogen bonds, Van der Waals force, ionic force, covalent linkages, and combinations thereof. The state of proximity between the interacting domains or entities may be transient or permanent, reversible or irreversible. In any event, it is in contrast to and distinguishable from contact caused by natural random movement of two entities. Typically although not necessarily, an "interaction" is exhibited by the binding between the interacting domains or entities. Examples of interactions include specific interactions between antigen and antibody, ligand and receptor, enzyme and substrate, and the like.

An "interaction" between two protein domains or complete proteins can be determined by a number of methods. For example, an interaction can be determined by functional assays such as the two-hybrid systems. Protein-protein interactions can also be determined by various biochemical approaches based on the affinity binding between two interacting partners. Such biochemical methods generally known in the art include, but are not limited to, protein affinity chromatography, affinity blotting, immunoprecipitation, and the like. The binding constant for two interacting proteins, which reflects the strength or quality of the interaction, can also be determined using methods known in the art. See Phizicky and Fields, *Microbiol. Rev.*, 59:94–123 (1995).

The terms "hybrid protein," "hybrid polypeptide," "hybrid peptide," "fusion protein," "fusion polypeptide," and "fusion peptide" are used herein interchangeably to mean a non-naturally occurring protein having a specified polypeptide molecule covalently linked to one or more polypeptide molecules that are not naturally linked to the specified polypeptide. Thus, for example, a "hybrid protein" may be two naturally occurring proteins or fragments thereof linked together by a covalent linkage. A "hybrid protein" may also be a protein formed by covalently linking two artificial polypeptides together. Typically but not necessarily, the two or more polypeptide molecules are "fused" together by a peptide bond, or linked indirectly via a linker moiety, forming a single non-branched polypeptide chain.

The term "chimeric gene" refers to a non-naturally occurring nucleic acid having covalently linked together two or more distinct portions that are not naturally linked directly to each other. Each "chimeric gene" encodes a fusion protein.

The term "test compound" as used herein encompasses all types of organic or inorganic molecules, including but not limited proteins, peptides, polysaccharides, lipids, nucleic acids, small organic molecules, inorganic compounds, and derivatives thereof.

As used herein, the terms "N-intein" and "C-intein" refer to an N-terminal and a C-terminal portion of an intein, respectively. An N-intein itself alone cannot direct protein splicing, and likewise, a C-intein itself alone is incapable of catalyzing protein splicing. However, when an N-intein and a C-intein are placed in close proximity, they are capable of acting in concert to catalyze protein trans-splicing. Conserved intein motifs have been identified in many inteins. Typically, an intein includes an N-terminal splicing region having sequence motifs designated A, $N_2$, B, and $N_4$, an endonuclease or linker domain region having sequence motifs designated C, D, E, and H, and a C-terminal splicing region having sequence motifs designated F and G. See Pietrokovski, *Protein Sci.*, 3:2340–2350 (1994); Pietrokovski, *Protein Sci.*, 7:64–71 (1998). Thus, in a specific embodiment, N-intein encompasses at least motifs A, $N_2$, B, and $N_4$, while C-intein includes at least motifs F and G. Typically, "N-intein" is an amino acid sequence matching the N-terminal sequence of about 90 to 110 amino acids of an intein, while "C-intein" is an amino acid sequence matching the C-terminal sequence of about 30 to 50 amino acids of an intein. A skilled artisan will recognize that optimal sequences of N-inteins and C-inteins can be determined by routine trial and error experiments. In addition, it should be understood that the terms "N-intein" and "C-intein" also encompass non-native or modified amino acid sequences that are derived from an N-terminal or C-terminal portion of an intein, respectively, e.g., modified or mutein forms containing amino acid insertions, deletions, or substitutions.

Protein precursors containing inteins have been found in all three life domains: archaea, bacteria, and eucarya. A large number of inteins exist in bacteria and a few found in yeast. See Perler et al., *Nucleic Acids Res.*, 28:1 344–5 (2000); see also *InBase, the New England Intein Database*, at http://www.neb.com/neb/inteins.html. The N-intein and C-intein used in the fusion proteins of the present invention can be selected according to the naturally occurring intein sequences. Alternatively, the naturally occurring intein sequences can be modified by deleting, inserting, or substituting amino acids to generate desirable properties in the N- and C-intein.

The term "functional" when used in connection with the MAT-alpha1p means that the MAT-alpha1p protein in a yeast haploid cell has activities sufficient to induce the expression of alpha-specific genes to the extent that yeast haploid cell exhibits alpha-mating type and can mate with an a-cell if other conditions permit. The term "functional" when used in connection with the MAT-alpha2p means that the MAT-alpha2p protein in a yeast haploid cell has activities sufficient to suppress the expression of a-specific genes to the extent that yeast haploid cell exhibits alpha-mating type and can mate with an a-cell if other conditions permit. Thus, when a yeast haploid cell is said to "lack a functional" MAT-alpha1p or MAT-alpha2p protein, it is intended to mean that the haploid cell does not express a functional MAT-alpha1p or MAT-alpha2p protein, or that the haploid cell expresses a defective MAT-alpha1p or MAT-alpha2p protein that is incapable of, respectively, inducing the expression of alpha-specific genes or suppressing the expression of a-specific genes to a sufficient extent to affect the mating type of the yeast haploid cell if other conditions permit.

The genetic basis of yeast mating control is well understood in the art. See e.g., Herskowitz et al., in *The Molecular and Cellular Biology of the Yeast Saccharomyces: Gene Expression*, Vol. 11, Jones et al., Ed., Cold Spring Harbor Laboratory Press, Cold Spring Harbor, N.Y., 1992. Essentially, yeast has two haploid mating types, a and alpha. Haploid cells of a-mating type mate with cells of alpha-mating type to form a/alpha cells. Cells of a-mating type express a-specific genes such as STE2, STE6, MFA1, MFA2, and BAR1, which are not expressed in alpha cells. Alpha cells express alpha-specific genes such as STE3, MFalpha1, and MFalpha2, which are not expressed in cells of a-mating type. The differential expression of the cell type-specific genes is determined by regulatory proteins including MATalpha1p, MATalpha2p, and MATa1p. In particular, the mating behavior of alpha cells is determined by the presence of the MATalpha locus. This locus encodes MATalpha1p, which is essential for the expression of alpha-specific genes, and MATalpha2p, which represses the expression of a-specific genes. A yeast haploid cell expressing both proteins exhibits the alpha-mating type, while inactivation of the two proteins causes a switch of the mating type from alpha to a. Yeast haploid cells expressing MATalpha2p but not MATalpha1p lack both the alpha-specific proteins and a-specific proteins, and thus are sterile. In addition, yeast haploid cells expressing MATalpha1p but not MATalpha2p can also be sterile.

The yeast two-hybrid system of the present invention utilizes the above regulatory scheme of yeast mating type determination. Essentially, two fusion proteins are recombinantly expressed in a test yeast haploid cell. One fusion protein contains one test polypeptide fused to an effector polypeptide, while the other fusion protein contains another test polypeptide fused to another effector polypeptide. The test yeast haploid cell is provided such that the expression of cell type-specific genes in the haploid cell is regulated by the synergistic action of the two effector polypeptides mediated by an interaction between the two test polypeptides in the two fusion proteins. As a result, the mating type of the test yeast haploid cell is determined by the presence or absence of a protein-protein interaction between the two test polypeptides. Thus, by determining whether the yeast haploid cell is capable of mating to form a yeast diploid cell in the presence or absence of one or more test compounds, the presence or absence of a protein-protein interaction between the two test polypeptides can be determined.

As will be apparent from the descriptions below, there can be many different embodiments of the method of the present invention. Any arrangements of the components in the fusion proteins, the mating-related genotypes, and optional relay genes and reporter genes can be adopted so long as a protein-protein interaction between the two test polypeptides or disruption thereof can be reflected in the mating type of the test yeast haploid cell or indicated by any alteration of the test yeast haploid cell's ability to mate.

Thus, in one embodiment, a yeast haploid cell of a- or alpha-mating type may be genetically modified such that either (1) a-specific genes are not expressed, and alpha-specific genes are controlled by synergistic action of the two effector polypeptides mediated by an interaction between the two test polypeptides; or (2) alpha-specific genes are not expressed, and a-specific genes are controlled by synergistic action of the two effector polypeptides mediated by an interaction between the two test polypeptides.

For example, an alpha type yeast haploid cell may be genetically engineered such that the expression of one or more of the alpha-specific genes (e.g., STE3, MFalpha1, and MFalpha2) that are essential for the cell to exhibit alpha-mating type is controlled by synergistic action of the two effector polypeptides mediated by an interaction between the two test polypeptides. Alternatively, a yeast haploid cell of a-mating type may be genetically engineered such that the expression of one or more of the a-specific genes (e.g., STE2, STE6, MFA1, MFA2, and BAR1) that are required for the cell to exhibit a-mating type are under the control of synergistic actions of the two effector polypeptides mediated by an interaction between the two test polypeptides.

The effector polypeptides can be domains that mediate DNA binding and transcriptional activation or repression. For example, one effector polypeptide can be a DNA binding domain, and the other effector polypeptide is a transcriptional activation domain or a transcriptional repressor domain. In this case, the open reading frame(s) of the alpha-specific gene(s) or a-specific gene(s) can be operably linked to a promoter having a recognition site for the DNA binding domain. Therefore, when the two test polypeptides interact with each other, the DNA binding domain and the transcriptional activation domain or the transcriptional repressor domain are brought into proximity, reconstituting a quasi-transcriptional activator or repressor. As a result, the transcription of the alpha-specific gene(s) or a-specific gene(s) is activated or repressed. See FIGS. 2A-2D.

Figure 2A:
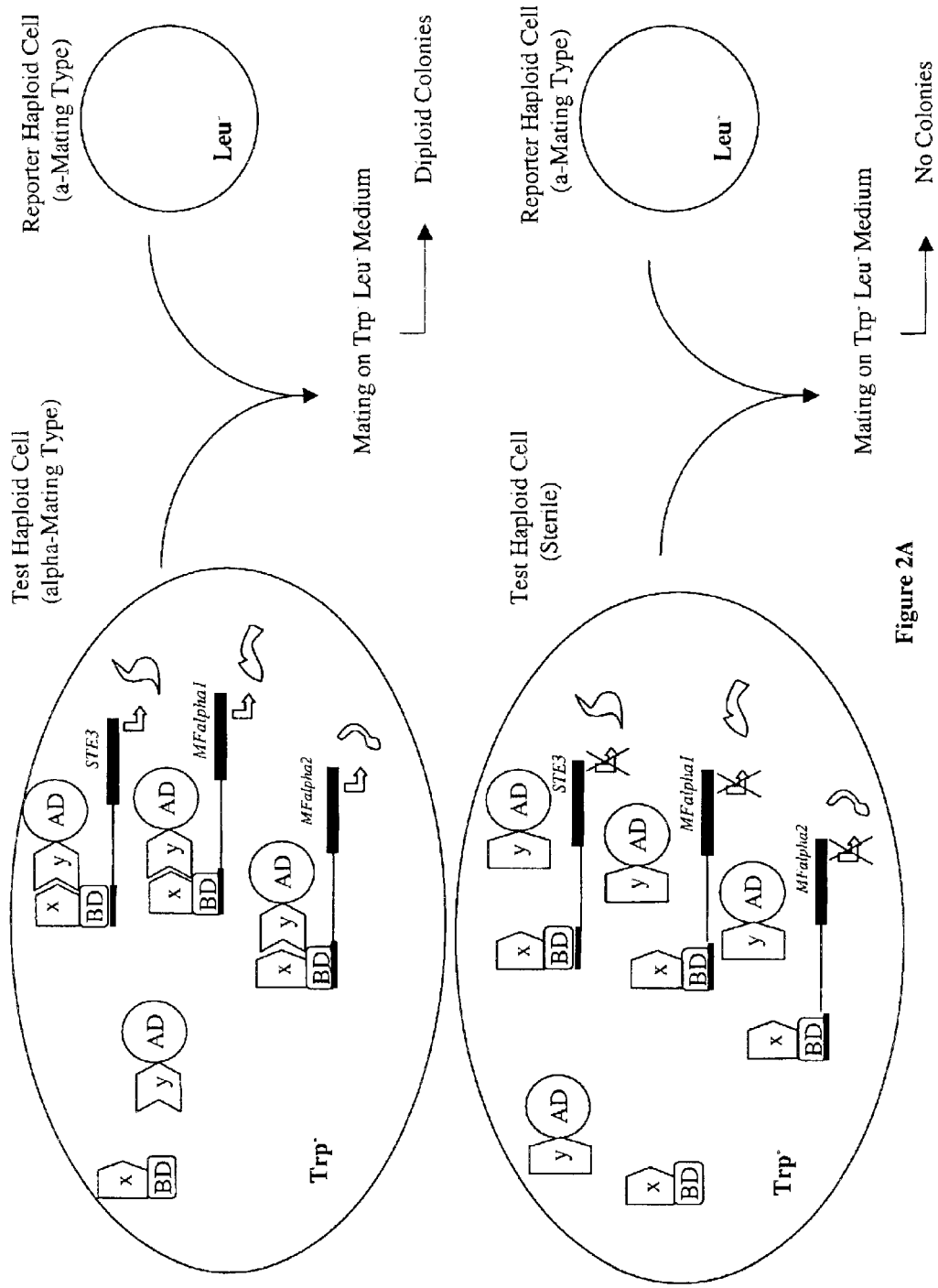
FIG. 2A is a diagram illustrating an embodiment of the present invention in which the expression of alpha-specific genes is under the control of the interaction between two test polypeptides in two fusion proteins, respectively.
Figure 2B:
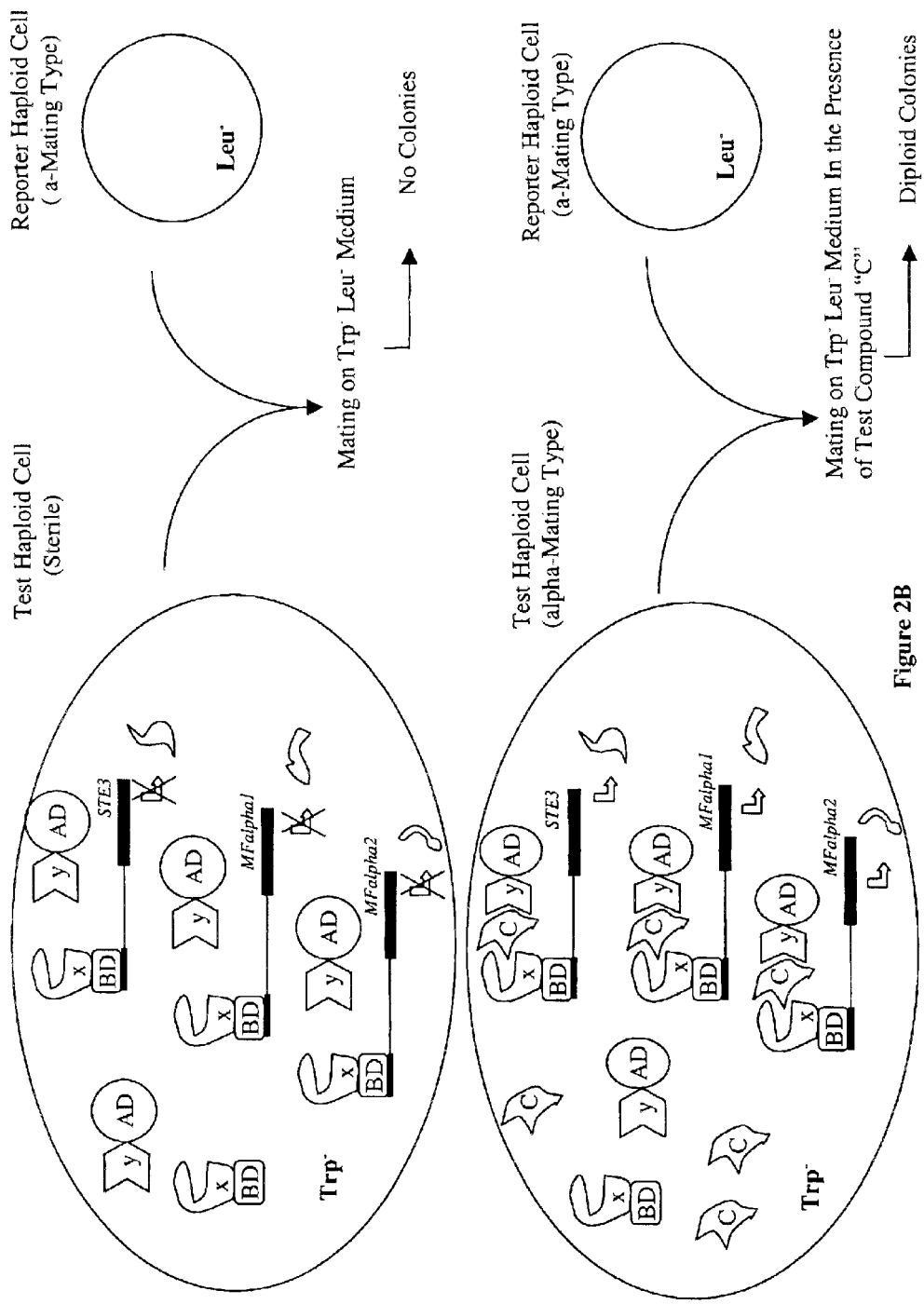
FIG. 2B shows an embodiment of the present invention in which a mating-based yeast two-hybrid system is designed to select compounds capable of initiating or strengthening a particular protein-protein interaction.

Thus, for example, one or more of the endogenous alpha-specific genes (STE3, MFalpha1, and MFalpha2) of an alpha yeast haploid cell can be knocked out by e.g., homologous recombination, and an exogenous version of the knocked-out gene(s) is introduced into the haploid cell. The exogenous gene(s) include a coding region operably linked to a promoter having a recognition site that is specific to the DNA binding domain in a fusion protein and is responsive to a transcriptional activation domain. Alternatively, one or more endogenous alpha-specific genes are recombinantly engineered to modify the promoter region such that each of the one or more endogenous coding regions is operably linked to a promoter having a recognition site that is specific to the DNA binding domain in a fusion protein and is responsive to a transcriptional activation domain. If the two test polypeptides interact with each other, the expression of the exogenous alpha-specific genes are activated causing the haploid cell to exhibit alpha-mating type. Accordingly, a diploid cell can be formed when the resulting alpha cell is co-cultured with a reporter yeast haploid cell of a-mating type. In the absence of an interaction between the two test polypeptides, the test yeast haploid cell is sterile. See FIG. 2A.

Where two test polypeptides are incapable of interacting with each other, the system shown in FIG. 2A can also be used to screen for compounds that are capable of initiating or strengthening the interaction between the two test polypeptides. Essentially, as shown in FIG. 2B, the mating-based two-hybrid system can be performed in the presence of one or more compounds. If a compound is capable of initiating or strengthening the interaction, the test yeast haploid cell exhibits alpha-mating type and can mate with an a-cell to form a diploid cell.

In a reverse system, a transcriptional repressor domain is used in the fusion protein in place of a transcriptional activation domain, and the expression of the alpha-specific genes is repressed by the repressor domain. Thus, when the two test polypeptides interact with each other, the expression of the alpha-specific genes are repressed and the haploid cell is sterile and incapable of mating. In contrast, when the interaction between the two test polypeptides is disrupted by, e.g., a test compound, the haploid cell switches to alpha-mating type and can mate with a cell of a-mating type. See FIG. 2C.

Figure 2C:
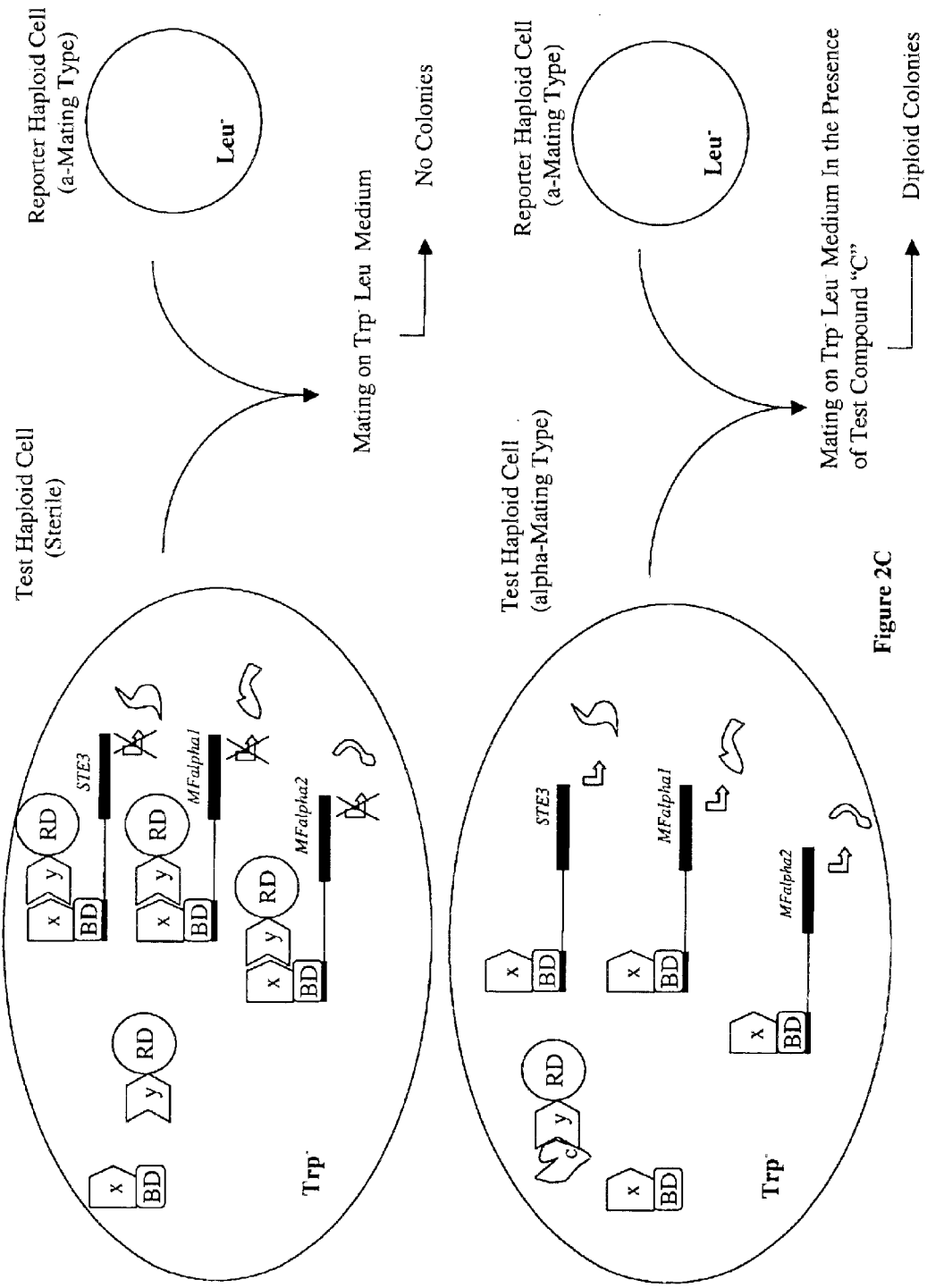
FIG. 2C is a schematic diagram demonstrating a reverse two-hybrid assay of the present invention in which the alpha-specific genes in a test haploid cell are expressed in the presence of a test compound capable of disrupting protein-protein interaction between two test polypeptides and as a result the cell exhibits alpha-mating type.
Figure 2D:
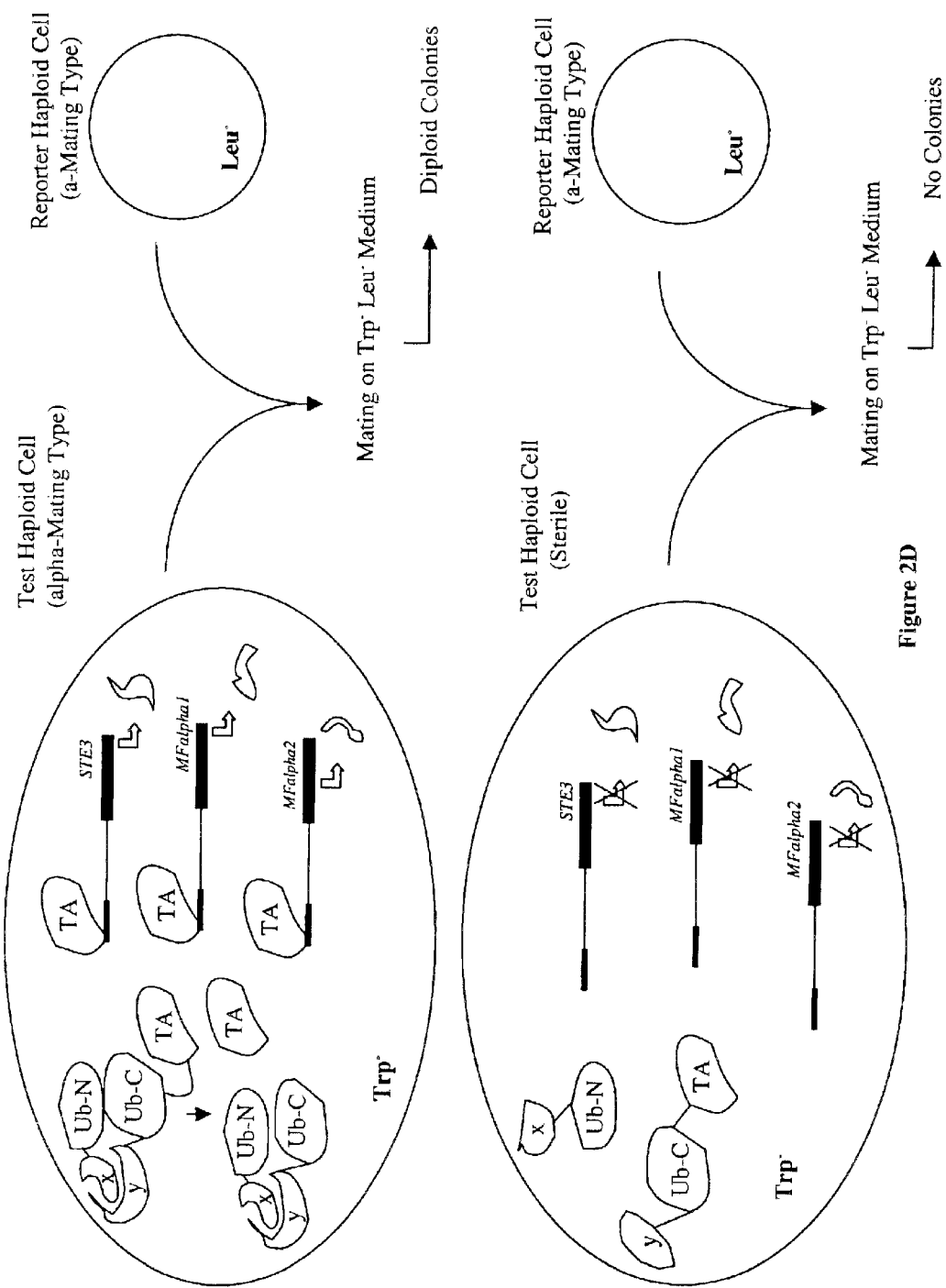
FIG. 2D shows another embodiment of the mating-based two-hybrid system of the present invention in which ubiquitin-based cleavage is utilized and a protein-protein interaction between two test polypeptides X and Y causes the release of a transcriptional activator TA, thus activating the alpha-specific genes in the test haploid cell.

Alternatively, the ubiquitin-based split protein sensor as disclosed in U.S. Pat. No. 5,585,245 (which is incorporated herein by reference in its entirety) can be used. That is, the effector polypeptides in the two fusion proteins are modified C-terminal subdomain and N-terminal subdomain of ubiquitin. For example, as shown in FIG. 2C, the endogenous alpha-specific genes (STE3, MFalpha1, and/or MFalpha2) of an alpha yeast haploid cell can be knocked out by e.g., homologous recombination, and an exogenous version of the genes is introduced into the haploid cell. The exogenous genes are placed under the control of a promoter inducible by a functional transcriptional activator, e.g., GAL4. Alternatively, the promoter regions of the endogenous alpha-specific genes are recombinantly engineered to replace the native promoters with promoters responsive to a transcriptional activation domain. In addition, two fusion proteins are expressed in the cell. One fusion protein comprises a modified N-terminal subdomain of ubiquitin linked to a test polypeptide, and the other fusion protein comprises a modified C-terminal subdomain of ubiquitin linked at its N-terminus to another test polypeptide and at its C-terminus to a transcriptional activator that can activate the expression of the exogenous or modified endogenous alpha-specific genes. The two ubiquitin subdomains are provided such that they do not reconstitute an active ubiquitin complex unless the two test polypeptides interact with each other. As disclosed in U.S. Pat. No. 5,585,245, the N-terminal subdomain of ubiquitin can be mutationally altered by replacing a first hydrophobic contact residue with a second residue side chain. For example, the either or both of the isoleucines at the $3^{rd}$ and $13^{th}$ codons of ubiquitin can be replaced with a glycine residue thus reducing the ability of the N-terminal and C-terminal subdomains of ubiquitin to interact with each other.

When the test polypeptides do interact with each other, a quasi-native ubiquitin complex is reconstituted which cleaves the fusion protein containing the transcriptional activator and releases a free and functional transcriptional activator, which in turn activates the expression of the alpha-specific genes. As a result, the haploid cell exhibits alpha-mating type and can be mated with an a-cell to form a diploid cell. See FIG. 2D.

Figure 2E:
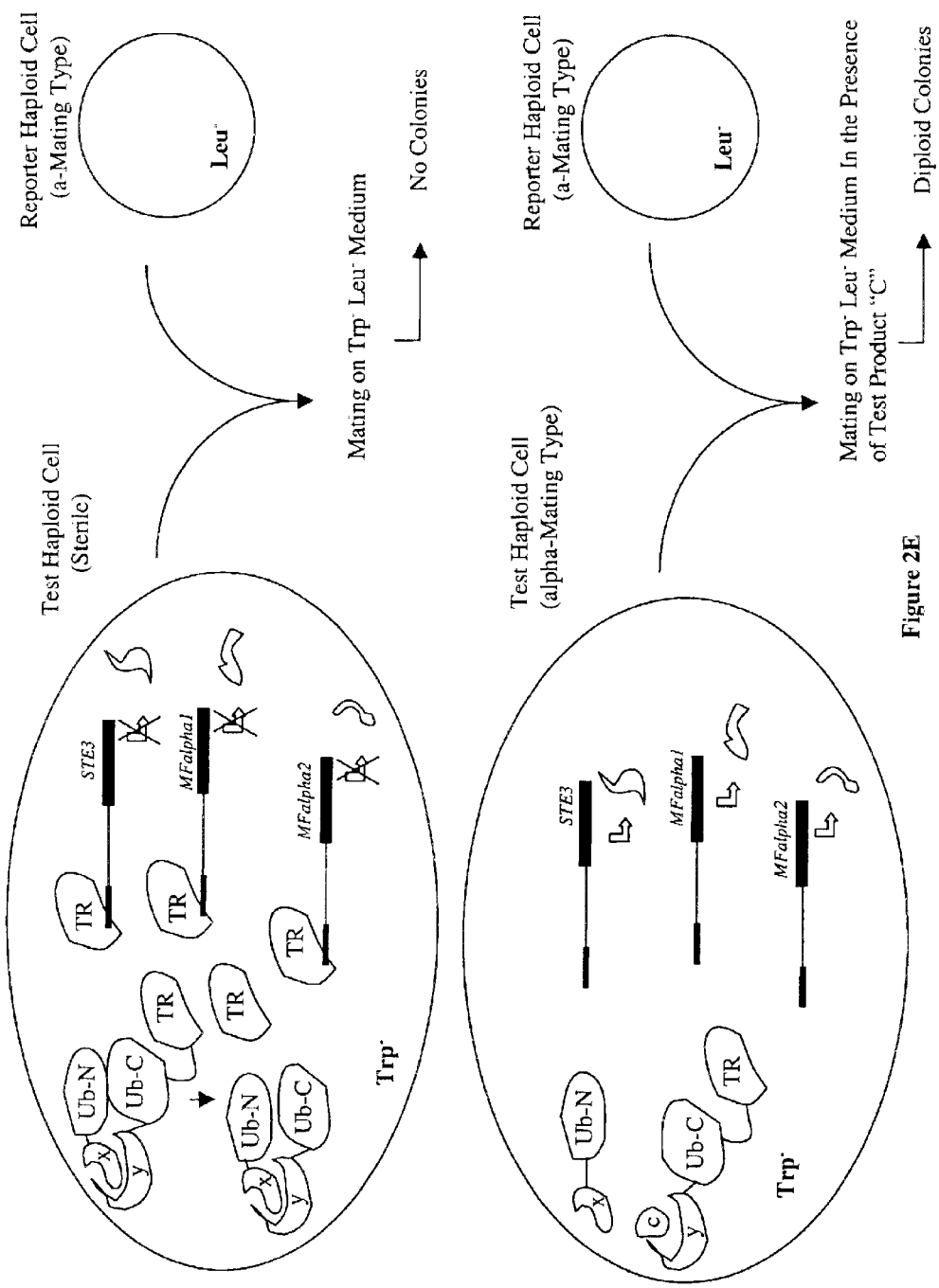
FIG. 2E shows another embodiment of the present invention which utilizes ubiquitin-based protein cleavage.

In a reverse system utilizing the ubiquitin-based method, a transcriptional repressor, e.g., GAL80, may be expressed in a fusion protein in place of the transcriptional activator described above in FIG. 2D. The alpha-specific genes are operably linked to promoters responsive to the transcriptional repressor. Thus, when the two test polypeptides interact with each other, the transcriptional repressor is released from one of the two fusion proteins and the expression of the alpha-specific genes is suppressed and the haploid cell is sterile. On the other hand, in the presence of a compound capable of disrupting the interaction between the two test polypeptides, the transcriptional repressor is not cleaved off and the alpha-specific genes are expressed causing the haploid cell to switch to alpha-mating type. The disruption of the interaction between the two test polypeptides can be detected based on the formation of diploid cells by the alpha cell and a reporter haploid cell of a-mating type. See FIG. 2E.

More preferably, instead of directly regulating the expression of the alpha-specific or a-specific genes by the interaction between two test polypeptides, the production of the mating-type regulatory proteins, specifically the production of functional MAT-alpha1p and/or MAT-alpha2p proteins, in a test yeast haploid cell is placed under the control of the interaction between two test polypeptides. Since the MAT-alpha1p and/or MAT-alpha2p proteins control the expression of the cell type-specific genes and cell mating type, the production of the MAT-alpha1p and/or MAT-alpha2p proteins determines cell mating type. Therefore, the presence or absence of an interaction between the two test polypeptides can also be detected based on mating behavior of the test yeast haploid cell.

In this scheme, two fusion proteins are recombinantly expressed in a test yeast haploid cell. One fusion protein contains a test polypeptide fused to an effector polypeptide, while the other fusion protein contains another test polypeptide fused to another effector polypeptide. The effector polypeptides can be, e.g., DNA binding domains, transcriptional activation domains or transcriptional repressor domains, or alternatively, a modified C-terminal subdomain or N-terminal subdomain of ubiquitin as disclosed in U.S. Pat. No. 5,585,245, which is incorporated herein by reference in its entirety. In addition, the effector polypeptides can also be inteins arranged in a way disclosed in commonly assigned U.S. patent application Ser. No. 10/040,910, U.S. Pat. No. 6,562,576 which is incorporated herein by reference. In any event, the interaction between the two test polypeptides results in the production of MAT-alpha1p and/or MAT-alpha2p and leads to mating type switching.

Thus, in one embodiment, the test yeast haploid cell expresses a functional MAT-alpha2p protein and the production of the MAT-alpha1p protein is determined by the presence or absence of an interaction between the two test polypeptides.

Figure 3A:
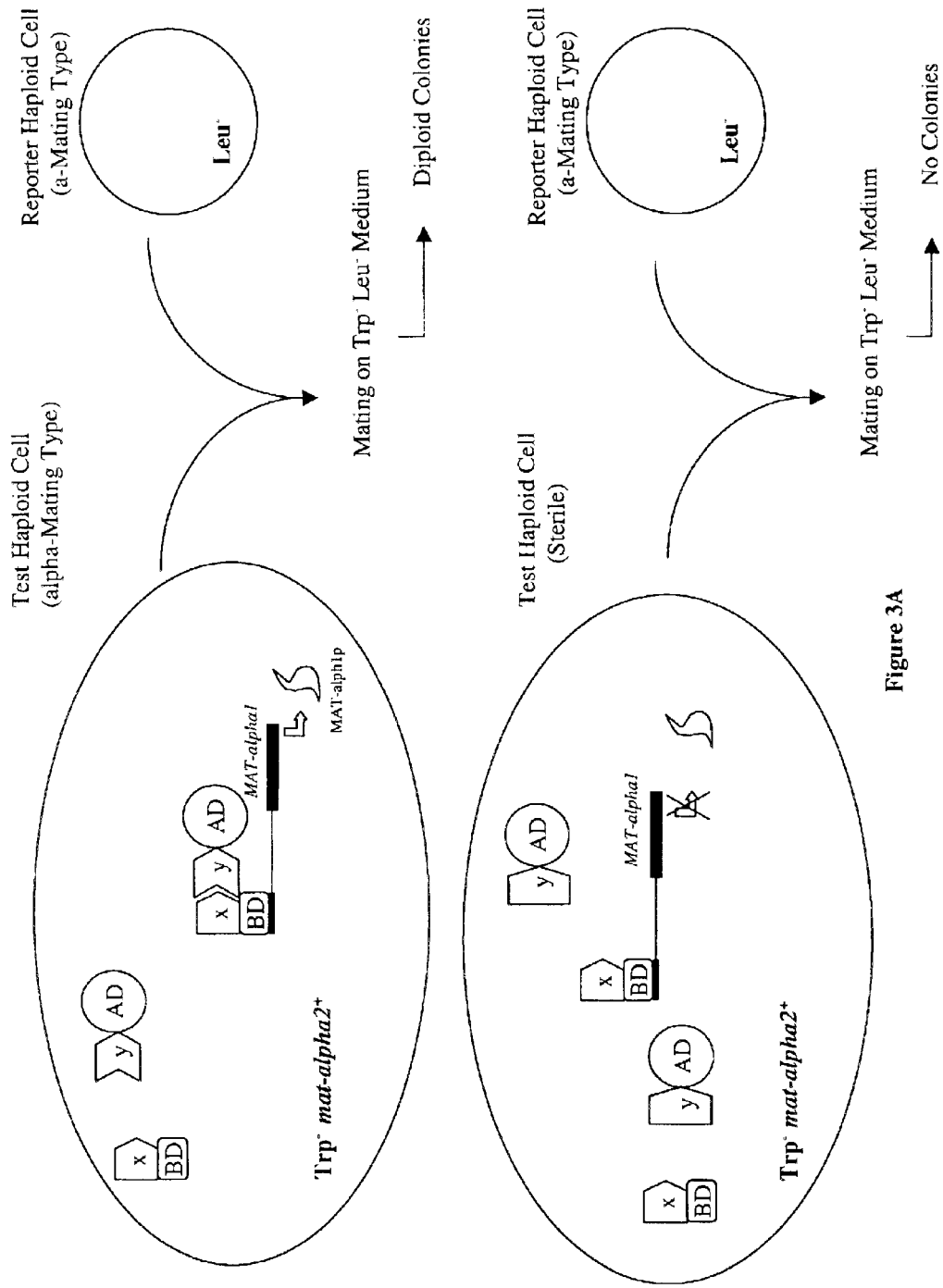
FIG. 3A illustrates another embodiment of the present invention in which the expression of the MAT-alpha1p protein in a test haploid cell is activated as a result of an interaction between the two test polypeptides X and Y.

For example, as shown in FIG. 3A, a test yeast haploid cell is provided wherein its MAT-alpha2 gene is normal while the transcription of the MAT-alpha1 gene is under the control of an inducible promoter. This can be done by knocking out the endogenous MAT-alpha1 gene in an alpha yeast haploid cell and introducing into the cell an exogenous construct having a MAT-alpha1 gene under the control of an inducible promoter, e.g., GAL1 promoter. Alternatively, the native MAT-alpha1 gene promoter can be modified or replaced by an inducible promoter. In addition, two fusion proteins are recombinantly expressed in the test haploid cell: one contains a test polypeptide X fused to a DNA binding domain BD, and the other has a test polypeptide Y fused to a transcriptional activation domain (AD). The inducible promoter has a recognition site that is specific to the DNA binding domain BD. When the BD and AD are brought together, they reconstitute a quasi-native transcriptional activator which activates the expression of the MAT-alpha1 gene, thus leading to the production of the MAT-alpha1p protein in the cell. Therefore, while the a-specific genes in the test haploid cell are repressed, the alpha-specific genes are induced by the functional MAT-alpha1p. As a result, the test yeast haploid cell exhibits alpha-mating type and can be mated with an a-cell to form a diploid cell. In contrast, in the absence an interaction between the two test polypeptides, no MAT-alpha1p protein is produced in the test haploid cell and the cell is sterile.

Figure 3B:
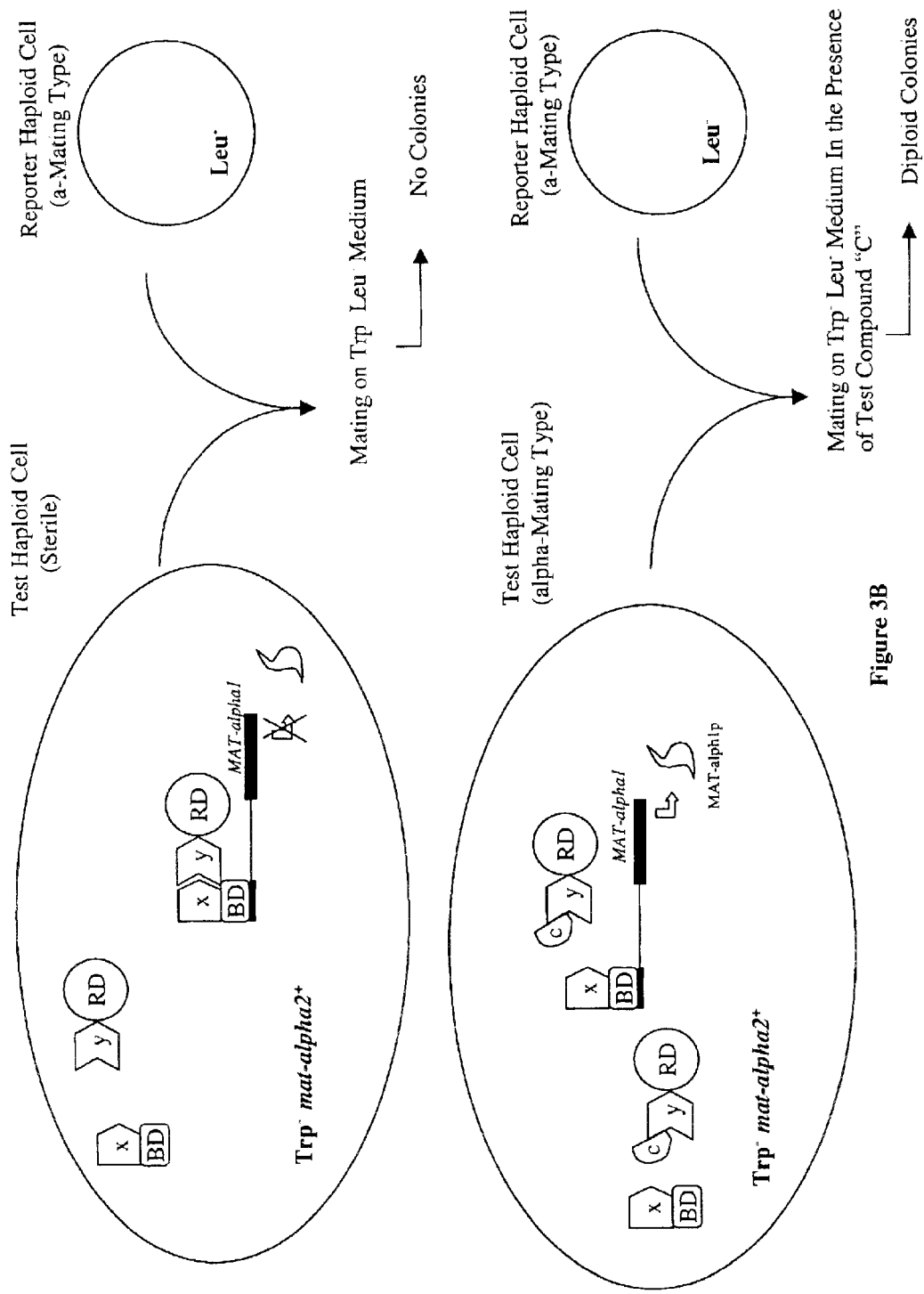
FIG. 3B shows an embodiment of the present invention in which the expression of the MAT-alpha1p protein in a test haploid cell is repressed as a result of an interaction between the two test polypeptides X and Y.

This system can be slightly modified to provide a reverse two-hybrid system. As shown in FIG. 3B, for example, a transcriptional repressor domain (RD) may be used in place of the AD, and the MAT-alpha1 gene is under the control of a promoter responsive to the reconstitution of a transcriptional repressor from the BD and the RD. Thus, in the presence of an interaction between the two test polypeptides, the MAT-alpha1 gene is repressed. No MAT-alpha1p protein is produced and the test yeast haploid cell does not express alpha-specific genes or a-specific genes, and is sterile. On the other hand, when the interaction is disrupted by a compound, the expression of the MAT-alpha1 gene is not suppressed and MAT-alpha1p protein is produced inducing the expression of the alpha-specific genes. As a result, the test haploid cell exhibits alpha-mating type and can mate with an a-cell to form a diploid cell.

Figure 3C:
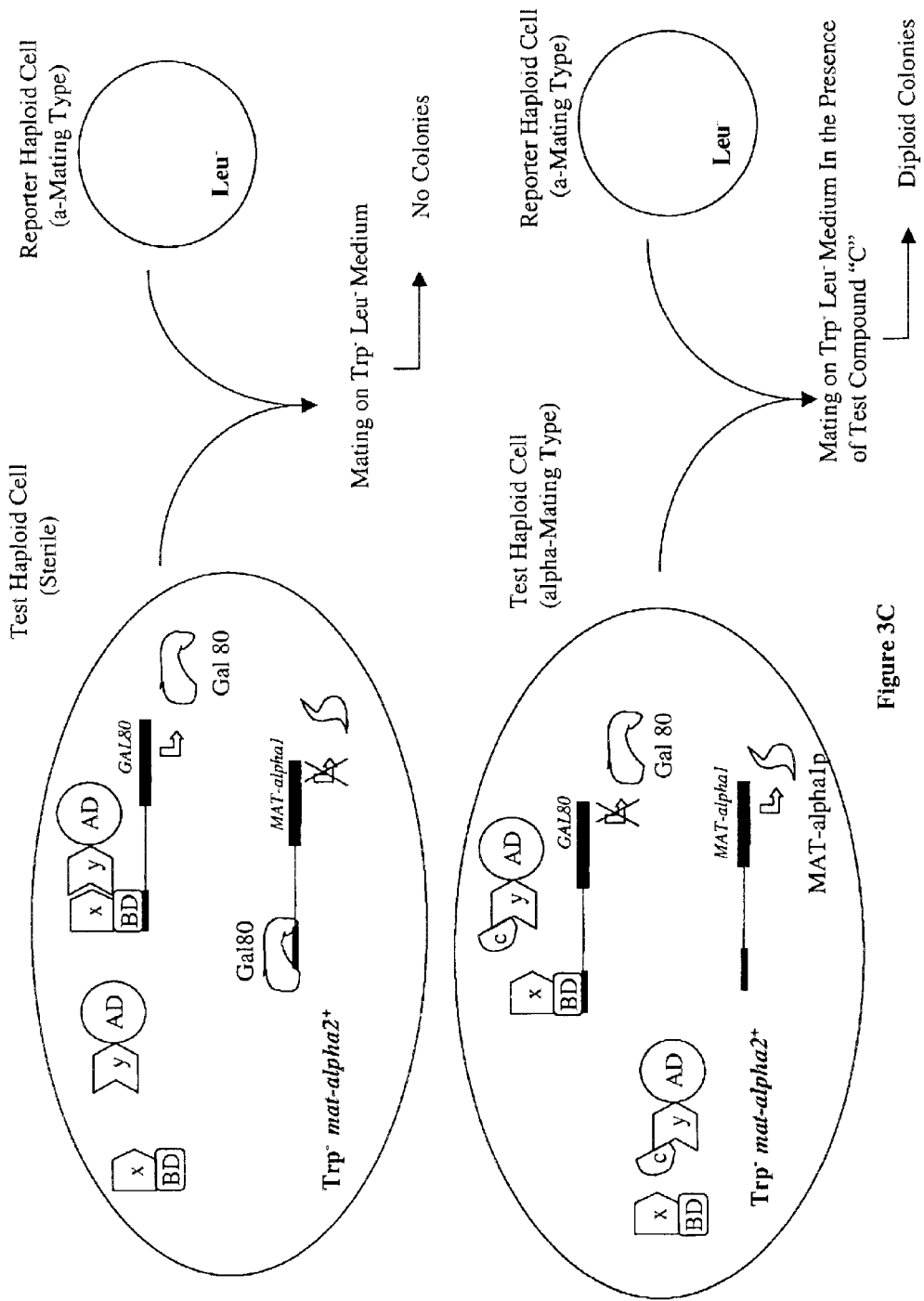
FIG. 3C is a schematic diagram demonstrating a reverse two-hybrid assay of the present invention in which the test haploid cell exhibits alpha-mating type in the presence of a test compound capable of disrupting the protein-protein interaction between the two test polypeptides.

FIG. 3C shows a variation of the system in FIG. 3B. Basically, two fusion proteins are expressed in a test yeast haploid cell, one having a test polypeptide X fused to a DNA binding domain (BD) and the other containing another test polypeptide Y fused to a transcriptional activation domain (AD). A relay gene is used whose transcription is activated by the quasi-native transcriptional activator reconstituted from the DNA binding domain (BD) and the transcriptional activation domain (AD) when the two test polypeptides interact with each other. The relay gene encodes a transcriptional repressor protein, e.g., GAL80. The use of relay gene in a reverse yeast two-hybrid system is disclosed in U.S. Pat. No. 5,525,490, which is incorporated herein by reference. In addition, the test yeast haploid cell also contains a reporter gene encoding the MAT-alpha1p protein. The reporter gene is driven by a promoter that is responsive to the transcriptional repressor encoded by the relay gene. The test yeast haploid cell should be engineered such that MAT-alpha1p protein can only be expressed from the reporter gene. Thus, when the two test polypeptides interact, the transcriptional repressor is expressed and the expression of the MAT-alpha1p protein is suppressed. As a result, the test yeast haploid cell does not express the alpha-specific genes or the a-specific genes and is thus sterile. In contrast, in the presence of a compound capable of interfering with or disrupting the interaction between the two test polypeptides, the expression of the reporter gene is not suppressed and MAT-alpha1p is produced. As a result, the test haploid cell exhibits alpha-mating type and is capable of mating with a reporter haploid cell of a-mating type. See FIG. 3C.

Figure 3D:
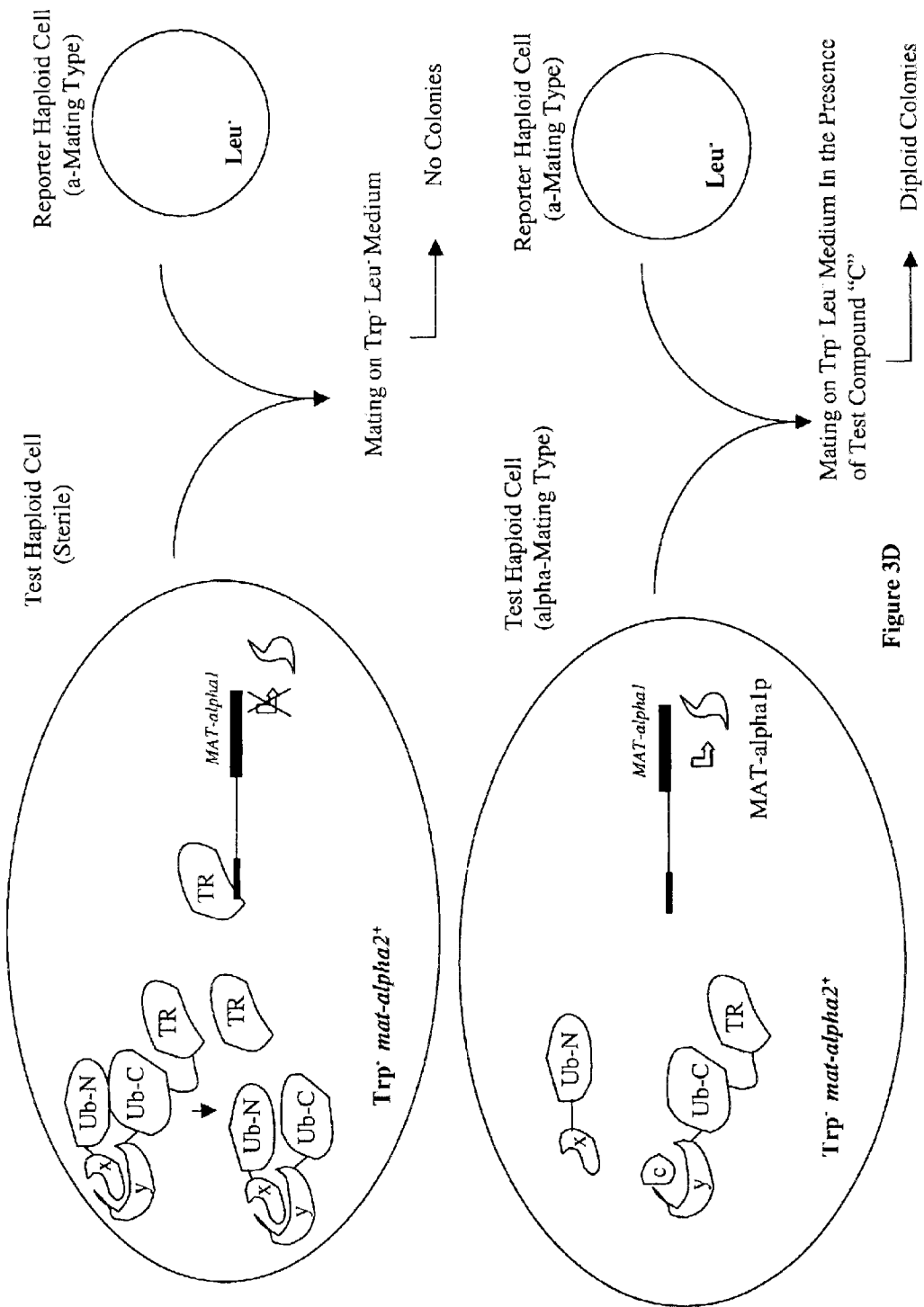
FIG. 3D illustrates another reverse two-hybrid assay of the present invention in which ubiquitin-based protein cleavage is utilized and the test haploid cell exhibits alpha-mating type in the in the presence of a test compound capable of disrupting the protein-protein interaction between the two test polypeptides.

A variation of the system illustrated in FIG. 3C is shown in FIG. 3D. Essentially, instead of the transcriptional control of the expression of the transcriptional repressor, the production of the transcriptional repressor is regulated by a quasi-native ubiquitin-based system disclosed in U.S. Pat. No. 5,585,245. That is, the fusion proteins in the system of FIG. 3C are replaced with two different fusion proteins, one fusion protein comprising a modified N-terminal subdomain of ubiquitin linked to one test polypeptide, and the other fusion protein having a modified C-terminal subdomain of ubiquitin linked at its N-terminus to another test polypeptide and at its C-terminus to the transcriptional repressor. Thus, in the presence of an interaction between the two test polypeptides, the transcriptional repressor is released from the fusion protein and suppresses the expression of the reporter gene. As a result, the MAT-alpha1p protein is not produced and the test haploid cell is sterile. In contrast, when the protein-protein interaction is disrupted by a compound, the repressor is not produced and MAT-alpha1p is produced. Thus, the haploid cell exhibits alpha-mating type.

Figure 3E:
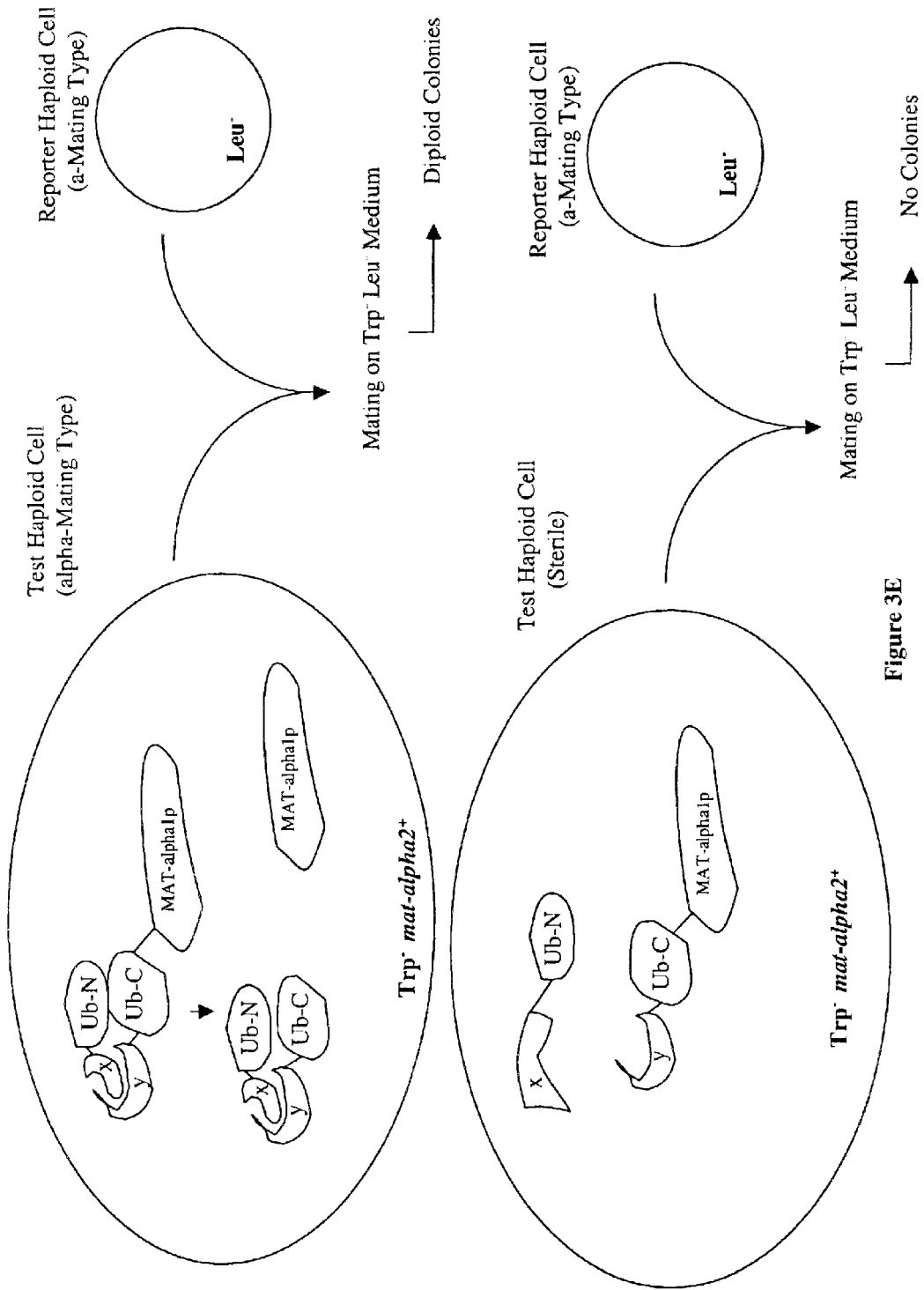
FIG. 3E shows another embodiment of the present invention in which ubiquitin-based protein cleavage is utilized to generate a free and functional MAT-alpha1p protein in the presence of an interaction between the two test polypeptides X and Y.

FIG. 3E illustrates a variation of the system shown in FIG. 3A. That is, in a test yeast haploid cell having a normal and functional MAT-alpha2p protein, the effector polypeptides in the two fusion proteins are modified C-terminal subdomain and N-terminal subdomain of ubiquitin, respectively. In addition, a MAT-alpha1p protein is fused to the C-terminus of the C-terminal subdomain of ubiquitin. In other words, one fusion protein comprises an N-terminal subdomain of ubiquitin linked to a test polypeptide, and the other fusion protein has a C-terminal subdomain of ubiquitin linked at its N-terminus to another test polypeptide and at its C-terminus to the MAT-alpha1p protein. Thus, in the presence of an interaction between the two test polypeptides, the MAT-alpha1p protein is cleaved off and alpha-specific genes are expressed in the test haploid cell. As a result, the haploid cell is switched to alpha-mating type and is capable of mating with an a-cell.

In yet another embodiment, the effector polypeptides can also be inteins arranged in a way disclosed in commonly assigned U.S. patent application Ser. No. 10/040,910, now U.S. Pat. No. 6,562,576 which is incorporated herein by reference. For example, the MAT-alpha1p protein can be divided into two portions. One fusion protein can include an N-intein linked to the C-terminus of the N-terminal portion of MAT-alpha1p and one test polypeptide fused to the C-terminus of the N-intein, while the other fusion protein includes a C-intein fused to the C-terminus of another test polypeptide and the C-terminal portion of MAT-alpha1p fused to the C-terminus of the C-intein. The two fusion proteins are expressed in a yeast haploid cell which expresses a functional MAT-alpha2p but lacks a functional MAT-alpha1p. In the presence of an interaction between the two test polypeptides, intein-based protein splicing occurs producing a functional MAT-alpha1p protein. As a result, the test yeast haploid cell exhibits the alpha-mating type and is capable of mating with a yeast haploid cell of a-mating type.

In another example, portions of a transcriptional activator or repressor may be used in the two fusion proteins described above in lieu of the MAT-alpha1p protein. Thus, the interaction between the two test polypeptides results in intein-based splicing leading to the production of a functional transcriptional activator or repressor, which in turn may activate or repress the expression of a reporter gene encoding, e.g., a functional MAT-alpha1p protein.

In another scheme, the test yeast haploid cell lacks a functional MAT-alpha1p protein and the production of the MAT-alpha2p protein is determined by the presence or absence of an interaction between two test polypeptides. In the test yeast haploid cell, the MAT-alpha1 gene may be knocked out or deleted such that it is not transcribed or translated. Alternatively, mutations may be introduced into the endogenous MAT-alpha1 gene such that the mutated gene encodes a protein that is defective in inducing the expression of alpha-specific genes in the test haploid cell.

Figure 4A:
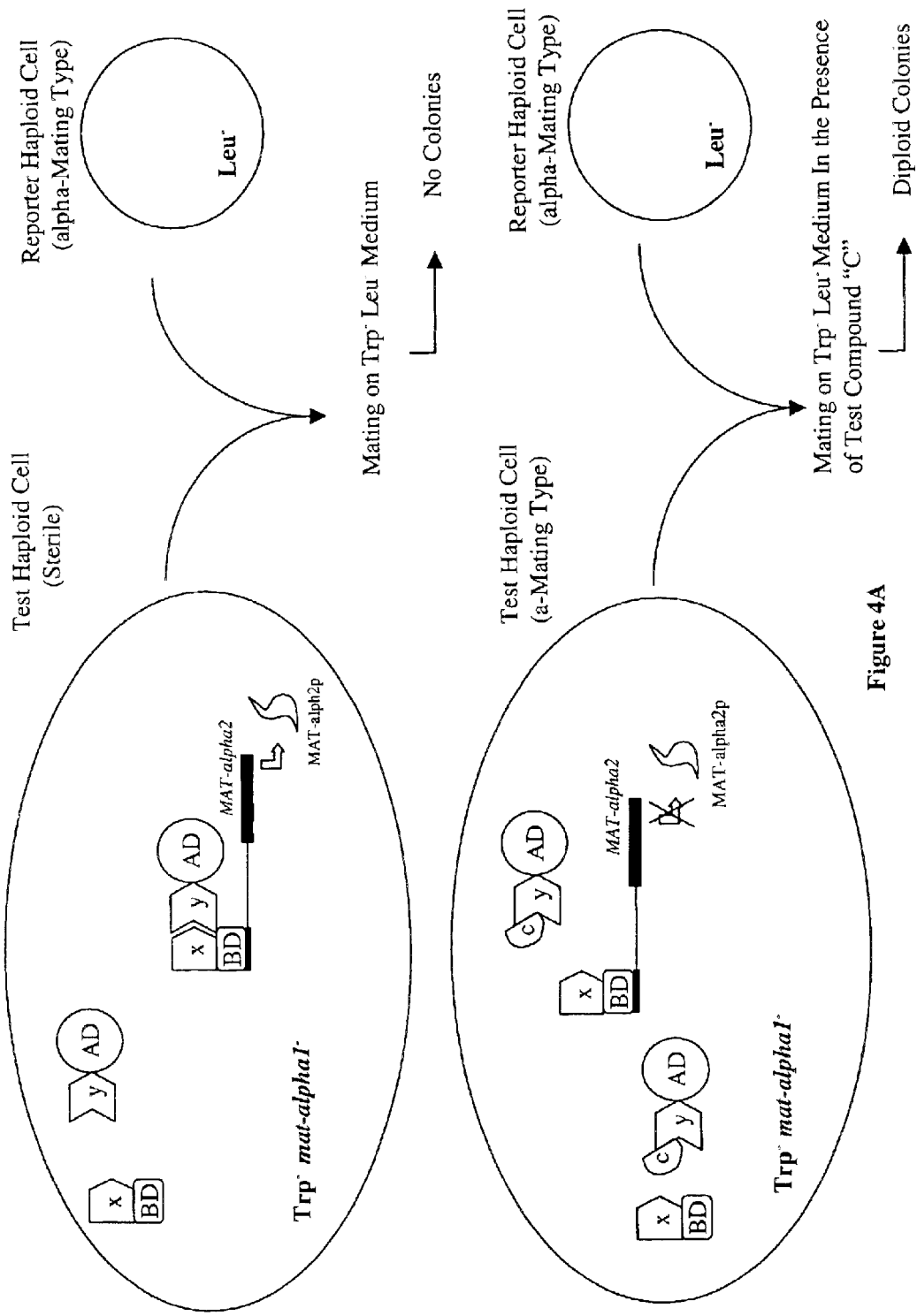
FIG. 4A illustrates a reverse two-hybrid assay of the present invention utilizing a test haploid cell with a mat-alpha1⁻ genotype wherein mating of the test haploid cell with an alpha-reporter haploid cell occurs only in the presence of a test compound capable of disrupting the interaction between the two test polypeptides X and Y.

For example, as shown in FIG. 4A, a test yeast haploid cell is provided which does not express a functional MAT-alpha1p protein. That is, the alpha-specific genes will not be expressed in the cell. The transcription of the MAT-alpha2 gene is under the control of an inducible promoter. This can be done by knocking out both the endogenous MAT-alpha2 gene and MAT-alpha1 gene in an alpha yeast haploid cell and introducing into the cell an exogenous construct having a MAT-alpha2 gene under the control of an inducible promoter, e.g., GAL1 promoter. Alternatively, the endogenous MAT-alpha1 gene is knocked out and the native MAT-alpha2 gene promoter can be modified or replaced by an inducible promoter. In addition, two fusion proteins are recombinantly expressed in the test haploid cell: one contains a test polypeptide X fused to a DNA binding domain BD, and the other has a test polypeptide Y fused to a transcriptional activation domain (AD). The inducible promoter has a recognition site specific to the DNA binding domain BD. When the BD and AD are brought together, they reconstitute a quasi-native transcriptional activator which activates the expression of the MAT-alpha2 gene thus producing the MAT-alpha2p protein. Therefore, the a-specific genes in the test haploid cell are repressed and the cell is sterile. In contrast, in the absence an interaction between the two test polypeptides, e.g., due to disruption by a test compound, no MAT-alpha2p protein is produced in the haploid cell. Thus, a-specific genes are expressed and the test haploid cell is an a-cell capable of mating with an alpha-cell.

Figure 4B:
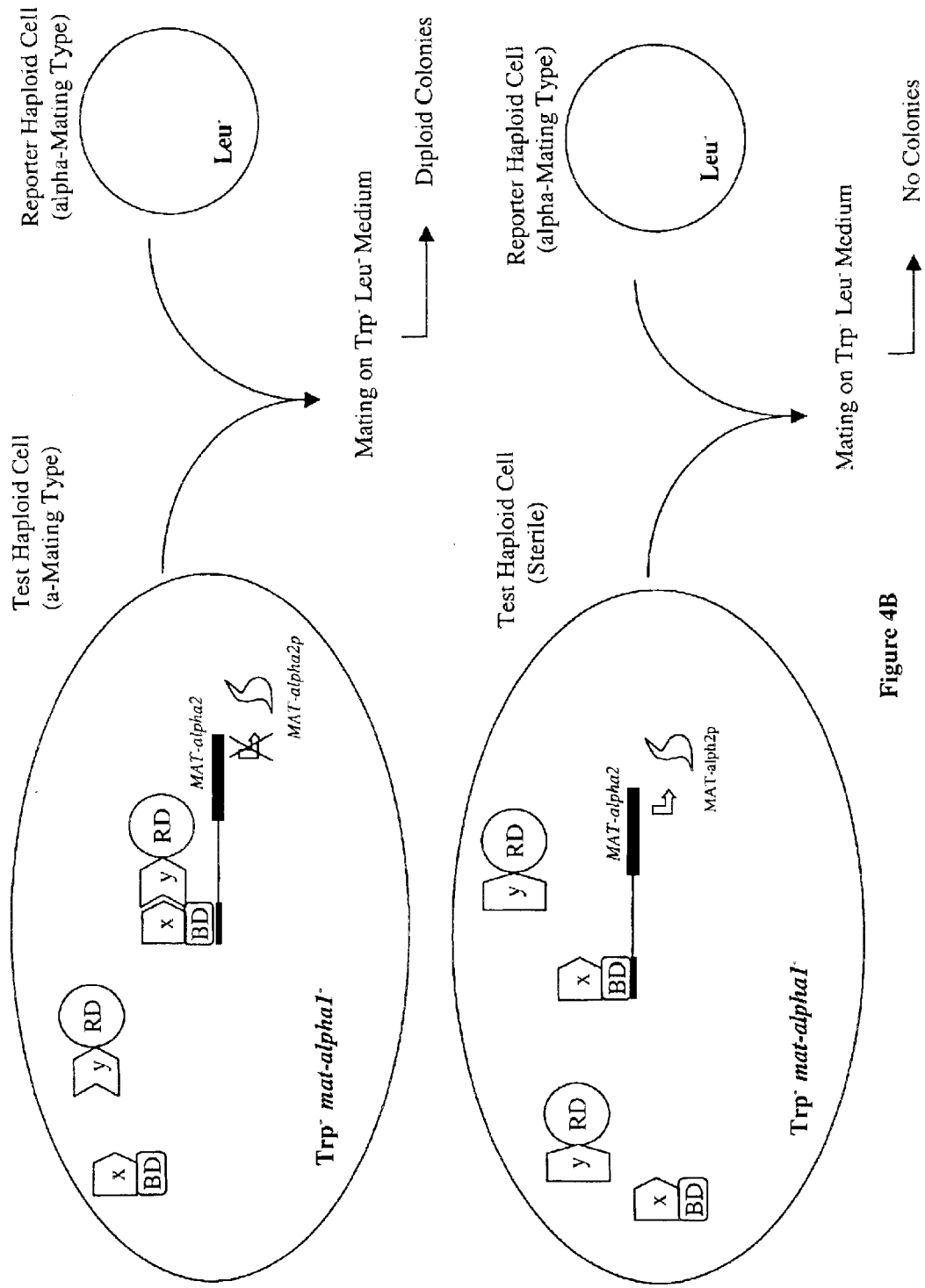
FIG. 4B is a schematic diagram illustrating an embodiment of the present invention in which a test haploid cell exhibits a-mating type in the presence of an interaction between the two test polypeptides X and Y.

This system can be modified to provide another two-hybrid system. As shown in FIG. 4B, for example, a transcriptional repressor domain (RD) may be used in place of the AD, and the MAT-alpha2 gene is under the control of a promoter responsive to the reconstitution of a quasi-native transcriptional repressor from the BD and the RD. Thus, in the presence of an interaction between the two test polypeptides, the MAT-alpha2 gene is repressed. No MAT-alpha2p protein is produced and the test haploid cell expresses a-specific genes and exhibits a-mating type. Thus, the cell can be mated with an alpha-cell to form a diploid cell. On the other hand, in the absence of the interaction, the expression of the MAT-alpha2 gene is not suppressed and MAT-alpha2p protein is produced suppressing the expression of the a-specific genes. As a result, the haploid cell is sterile.

Figure 4C:
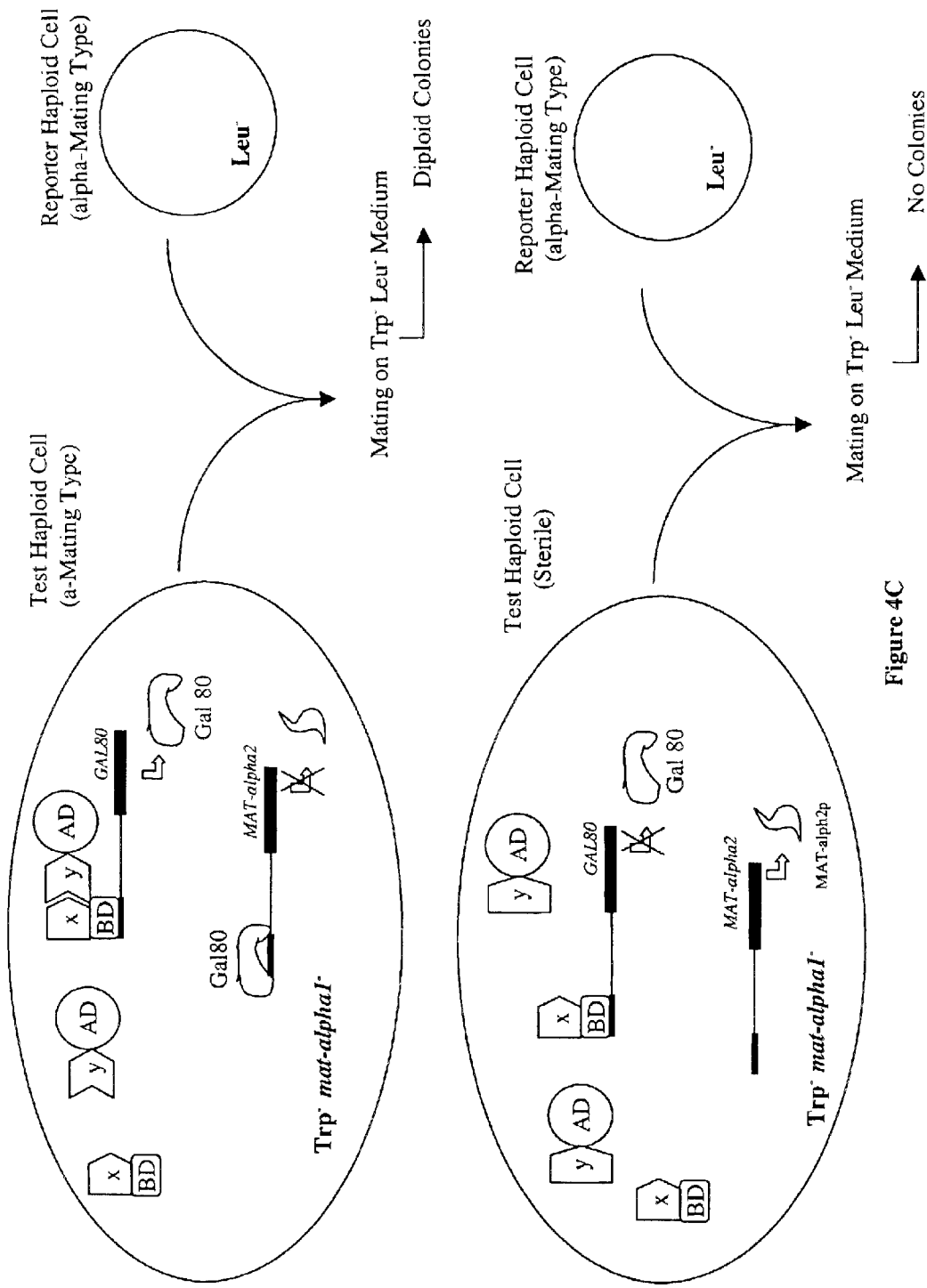
FIG. 4C is another schematic diagram for an embodiment of the present invention in which MAT-alpha2 gene is suppressed and the test haploid cell exhibits a-mating type when the two test polypeptides X and Y can interact with each other.

FIG. 4C shows a variation of the system in FIG. 4B. Two fusion proteins are expressed in a test yeast haploid cell, one having a test polypeptide X fused to a DNA binding domain (BD) and the other containing another test polypeptide Y fused to a transcriptional activation domain (AD). A relay gene is used whose transcription is activated by the quasi-native transcriptional activator reconstituted from the DNA binding domain (BD) and the transcriptional activation domain (AD) when the two test polypeptides interact with each other. The relay gene encodes a transcriptional repressor protein, e.g., GAL80. In addition, the test yeast haploid cell also contains a reporter gene encoding the MAT-alpha2p protein. The reporter gene is driven by a promoter that is responsive to the transcriptional repressor encoded by the relay gene. The yeast haploid cell should be engineered such that it does not express a functional MAT-alpha1p protein and the only MAT-alpha2p protein is expressed from the reporter gene. Thus, when the two test polypeptides interact, the transcriptional repressor is expressed and the expression of the MAT-alpha2p protein is suppressed. As a result, the test yeast haploid cell expresses the a-specific genes and exhibits a-mating type. A reporter yeast haploid cell of alpha-mating type can be mated with the test yeast haploid cell to form a diploid cell. In the absence of an interaction between the two test polypeptides, the expression of the reporter gene is not suppressed and MAT-alpha2p is produced. As a result, the haploid cell is sterile. In the alternative, the relay gene can encode a transcriptional activator and the reporter gene encoding the MAT-alpha2p protein has a promoter responsive to the transcriptional activator.

Figure 4D:
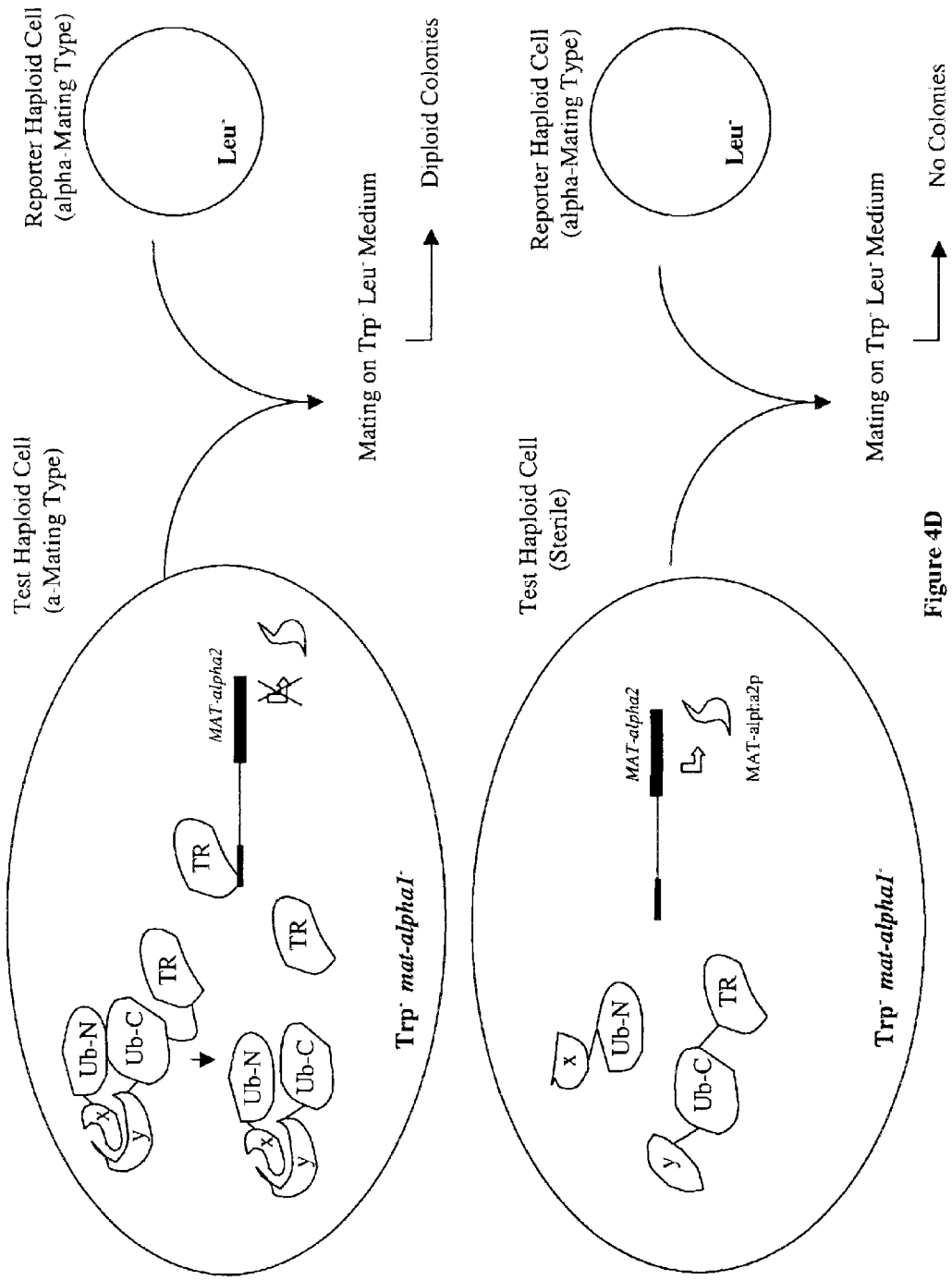
FIG. 4D demonstrates another embodiment of the present invention in which ubiquitin-based protein cleavage is employed to release a free and functional transcriptional repressor in the presence of an interaction between the two test polypeptides X and Y, and as a result, the transcription of the MAT-alpha2 gene is suppressed.

A variation of the system illustrated in FIG. 4C is shown in FIG. 4D. Again, the test haploid cell does not express a functional MAT-alpha1p protein. In principle, instead of the transcriptional control of the expression of the transcriptional repressor, the production of the transcriptional repressor is regulated by a quasi-native ubiquitin-based system disclosed in U.S. Pat. No. 5,585,245. That is, the fusion proteins in the system of FIG. 4C are replaced with two different fusion proteins, one fusion protein comprising a modified N-terminal subdomain of ubiquitin linked to one test polypeptide, and the other fusion protein having a modified C-terminal subdomain of ubiquitin linked at its N-terminus to another test polypeptide and at its C-terminus to the transcriptional repressor. Thus, in the presence of an interaction between the two test polypeptides, the transcriptional repressor is released from the fusion protein and suppresses the expression of the reporter gene. As a result, the MAT-alpha2p protein is not produced and the haploid cell exhibits a-mating type. In contrast, in the absence of an interaction between the two test polypeptides, the repressor is not released and MAT-alpha2p is produced. Thus, the test haploid cell is sterile.

Figure 4E:
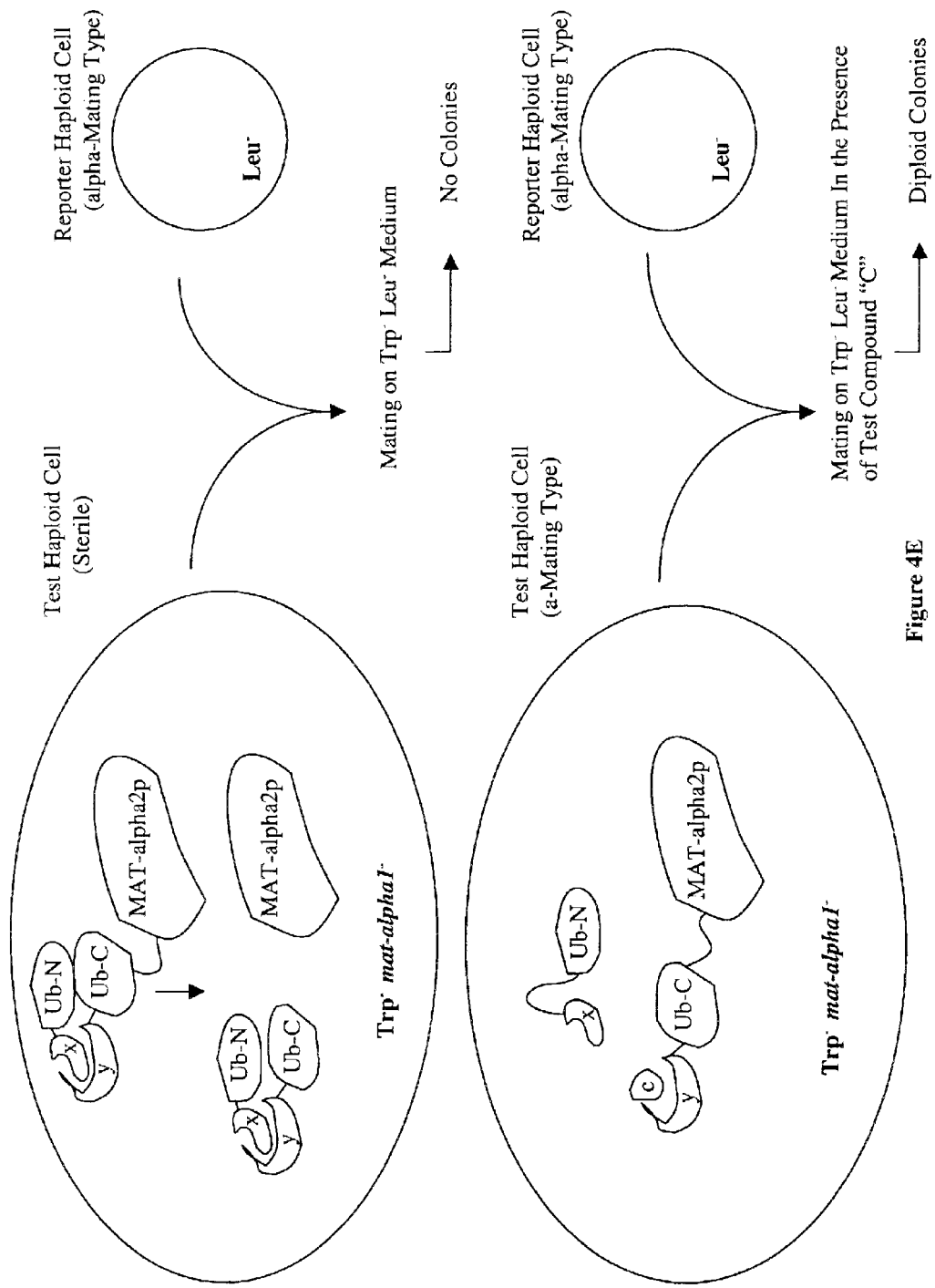
FIG. 4E shows a reverse two-hybrid system employing ubiquitin-based protein cleavage wherein the release of a free and functional MAT-alpha2p protein from a fusion protein is prevented in the presence of a test compound capable of interrupting the protein-protein interaction between the two test polypeptides X and Y, and as a result, the test haploid cell is able to mate with an alpha-reporter haploid cell in the presence of the test compound.

FIG. 4E illustrates a variation of the system shown in FIG. 4D. That is, in a test yeast haploid cell that lacks a functional MAT-alpha1p protein, the effector polypeptides in the two fusion proteins are modified C-terminal subdomain and N-terminal subdomain of ubiquitin, respectively. In addition, a MAT-alpha2p protein is fused to the C-terminus of the C-terminal subdomain. In other words, one fusion protein comprises an N-terminal subdomain of ubiquitin linked to one test polypeptide, and the other fusion protein has a C-terminal subdomain of ubiquitin linked at its N-terminus to another test polypeptide and at its C-terminus to the MAT-alpha2p protein. Thus, in the presence of an interaction between the two test polypeptides, the MAT-alpha2p protein is cleaved off and a-specific genes are not expressed in the haploid cell. As a result, the haploid cell is sterile. On the other hand, when the protein-protein interaction is disrupted, e.g., by a test compound, a MAT-alpha2p protein is not produced and a-specific genes are expressed. Thus, the haploid cell is switched to a-mating type and is capable of mating with an alpha-cell.

Figure 4F:
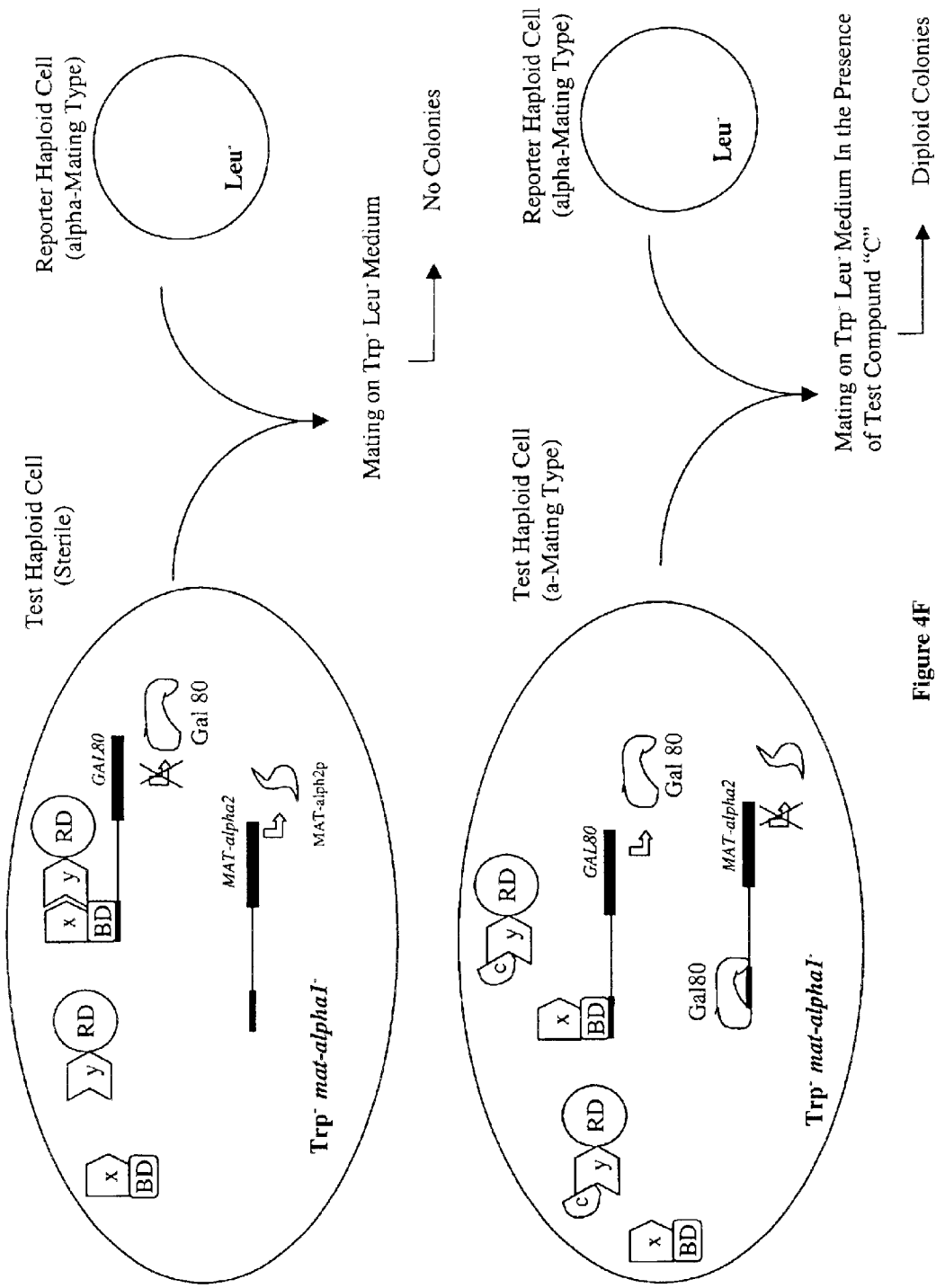
FIG. 4F is another reverse two-hybrid system in which the presence of a test compound capable of disrupting the interaction between two test polypeptides X and Y leads to the expression of a relay gene encoding a transcriptional repressor which in turn suppresses the expression of the MAT-alpha2 gene in the test yeast haploid cell lacking MAT-alpha1p, and as a result, the otherwise sterile haploid cell is switched to a-mating type.

FIG. 4F illustrates another reverse two-hybrid system of the present invention. In this scheme, the test haploid cell has a mat-alpha1⁻ genotype (i.e., lacks a functional MAT-alpha1p) and expresses two fusion proteins. One fusion protein includes a test polypeptide X and a DNA binding domain BD while another fusion protein includes a test polypeptide Y and a transcriptional repressor domain RD. The test yeast haploid cell further contains a relay gene encoding a transcriptional repressor (e.g., GAL80) and having a promoter capable of binding to the DNA binding domain in the test polypeptide X-containing fusion protein. In addition, the test yeast haploid cell also contains a reporter gene encoding MAT-alpha2p and having a promoter responsive to the transcriptional repressor encoded by the relay gene. It is noted that the promoter of the reporter gene should not be responsive to a quasi-native transcriptional repressor reconstituted from the interaction between X and Y in the two fusion proteins. Thus, when X and Y interact with each other bringing the BD and RD together thus reconstituting a quasi-native transcriptional repressor, the expression of the relay gene is suppressed and the transcriptional repressor encoded by the relay gene is not expressed. As a result, MAT-alpha2p is produced and the test haploid cell is sterile. On the contrary, in the presence of a test compound capable of disrupting the interaction between X and Y, the relay gene is expressed and the expression of the reporter gene is suppressed and no MAT-alpha2p protein is produced. As a result, the test yeast haploid cell is switched to a-mating type and can mate with a reporter haploid cell of alpha-mating type. The growth of diploid cells in a suitable selection medium selecting against the test and reporter yeast haploid cells would indicate the presence of a test compound capable of disrupting the interaction between X and Y.

Figure 4G:
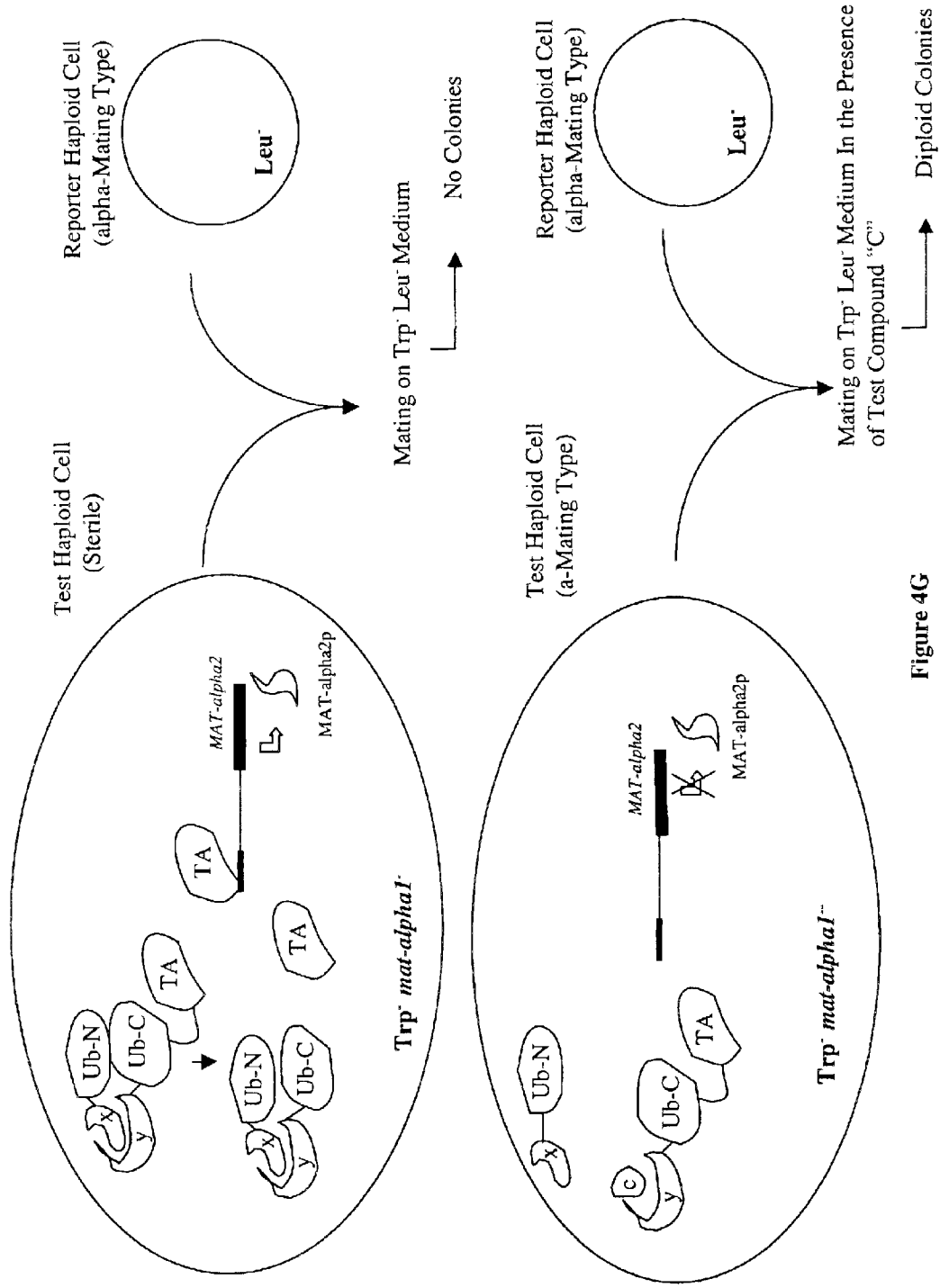
FIG. 4G illustrates yet another reverse two-hybrid system in which the presence of a test compound capable of disrupting the interaction between two test polypeptides X and Y prevents the release of a free and functional transcriptional activator from a fusion protein, and as a result, the expression of the MAT-alpha2 gene whose transcription depends on the transcriptional activator is not activated and the MAT-alpha1p-lacking test yeast haploid cell exhibits a-mating type.

FIG. 4G shows yet another reverse two-hybrid system in the background of a mat-alpha1[31] test yeast haploid cell. In this system, two fusion proteins are expressed in the mat-alpha1⁻ test yeast haploid cell. One fusion protein comprises a modified N-terminal subdomain of ubiquitin linked to one test polypeptide X, and another fusion protein has a modified C-terminal subdomain of ubiquitin linked at its N-terminus to another test polypeptide Y and at its C-terminus to a transcriptional activator TA. The test haploid cell further contains a reporter gene encoding MAT-alpha2p and having a promoter capable of binding to the transcriptional activator TA in the Y-containing fusion protein. Thus, in the presence of an interaction between the two test polypeptides, the transcriptional activator is released from the fusion protein and the expression of the reporter gene is activated. As a result, the MAT-alpha2p protein is produced and the test haploid cell is sterile. In contrast, when the protein-protein interaction is disrupted by a test compound, the transcriptional activator TA is not cleaved off from the Y-containing fusion protein, and MAT-alpha2 gene expression is not activated. Thus, the haploid cell exhibits a-mating type.

In yet another embodiment, the effector polypeptides can also be inteins arranged in a way disclosed in commonly assigned U.S. patent application Ser. No. 10/040,910, U.S. Pat. No. 6,562,576 which is incorporated herein by reference. For example, the MAT-alpha2p protein can be divided into two portions. One fusion protein can include an N-intein linked to the C-terminus of the N-terminal portion of MAT-alpha2p and one test polypeptide fused to the C-terminus of the N-intein, while the other fusion protein includes a C-intein fused to the C-terminus of another test polypeptide and the C-terminal portion of MAT-alpha2p fused to the C-terminus of the C-intein. The two fusion proteins are expressed in a yeast haploid cell which lacks endogenous functional MAT-alpha1p or MAT-alpha2p. In the presence of an interaction between the two test polypeptides, intein-based protein splicing leads to the formation of a functional MAT-alpha2p protein. As a result, the test yeast haploid cell is sterile. In contrast, in the absence of the interaction (e.g., due to disruption by a test compound), protein splicing does not occur and a functional MAT-alpha2p is not produced. Consequently, the test yeast haploid cell exhibits the a-mating type and is capable of mating with a yeast haploid cell of alpha-mating type.

In another example, portions of a transcriptional activator or repressor may be used in the two fusion proteins described above in lieu of the MAT-alpha2p protein. Thus, the interaction between the two test polypeptides results in intein-based splicing leading to the production of a functional transcriptional activator or repressor, which in turn may activate or repress the expression of a reporter gene encoding, e.g., a functional MAT-alpha2p protein.

As will be apparent to skilled artisans, there can be many other constructions of the system of the present invention other than those enumerated above. However, skilled artisans apprised of the present disclosure will be able to modify the above individual embodiments based on the teachings of the disclosure herein without undue experimentation. Such various modifications are intended to be encompassed by the present invention and are within the scope of the appended claims.

Apprised of the above disclosure on the various schemes of the system of the present invention, a skilled artisan should be able to construct the test yeast haploid cells useful in the system and select appropriate reporter yeast haploid cells using genetic and molecular biology methods known in the art.

Specifically, any yeast cells can be used so long as they have a mating regulatory machinery amenable to the mating-based schemes in the two-hybrid system of the present invention. Preferably, haploid cells of a yeast species within the genus of *Saccharomyces*, particularly *Saccharomyces cerevisiae*, are used as test yeast haploid cells and reporter yeast haploid cells. Other examples of suitable yeast species include, but are not limited to, *Hansenula polymorpha*, *Pichia pastoris*, and *Schizosaccharomyces pombe*. While a test yeast haploid cell expresses fusion proteins and one or more reporter genes, a reporter yeast haploid cell simply needs to exhibit either a- or alpha-mating type and have a suitable reporting marker as described below.

Numerous yeast strains or derivative strains are known in the art. Many of them have been developed specifically for certain yeast two-hybrid systems. The application and optional modification of such strains for purposes of the present invention should be apparent to a skilled artisan apprised of the present disclosure. Methods for genetically manipulating yeast strains using genetic crossing or recombinant mutagenesis are well known in the art. See e.g., Rothstein, *Meth. Enzymol.*, 101:202–211 (1983). By way of example, the following yeast strains are well known in the art, and can be used in the present invention upon necessary modifications and adjustment:

L40 strain which has the genotype MATαhis3Δ200 trp1–901 leu2–3,112 ade2 LYS2::(lexAop)4-HIS3 URA3::(lexAop)8-lacZ;

EGY48 strain which has the genotype MATα trp1 his3 ura3 6ops-LEU2; and

MaV103 strain which has the genotype MATα ura3–52 leu2–3,112 trp1–901 his3Δ200 ade2–101 gal4Δ gal80Δ SPAL10::URA3 GAL1::HIS3::lys2 (see Kuma *J. Biol. Chem.* 272:13548–13554 (1997); Vidal et al., *Proc. Natl. Acad. Sci. USA*, 93:10315–10320 (1996)). Such strains are generally available in the research community, and can also be obtained by simple yeast genetic manipulation. See, e.g., *The Yeast Two-Hybrid System*, Bartel and Fields, eds., pages 173–182, Oxford University Press, New York, N.Y., 1997.

In addition, the following yeast strains are commercially available:

Y190 strain which is available from Clontech, Palo Alto, Calif. and has the genotype MATαgal4 gal80 his3Δ200 trp1–901 ade2–101 ura3–52 leu2–3, 112 URA3::GAL1-lacZ LYS2::GAL1-HIS3 cyh$^r$; and YRG-2 Strain which is available from Stratagene, La Jolla, Calif. and has the genotype MATalpha ura3–52 his3–200 ade2–101 lys2–801 trp1–901 leu2–3, 112 gal80–538 LYS2::GAL1-HIS3 URA3::GAL1/CYC1-lacZ.

Either alpha- or a-cells available in the art can be modified to make an appropriate test yeast haploid cell. For example, to make a test yeast haploid cell that lacks a functional MAT-alpha1p or MAT-alpha2p protein or both, the full endogenous gene(s) or a portion thereof can be deleted by, e.g., homologous recombination. Alternatively, mutations can be introduced into the endogenous gene(s) in the coding region or a regulatory region such that the mutated endogenous gene(s) either do not express a protein or express a defective protein that is not functional. Mutations may be introduced by homologous recombination or any other techniques known in the art.

To express the fusion proteins in a test yeast haploid cell of the present invention, chimeric genes encoding the fusion proteins may be introduced into the yeast haploid cell by any suitable methods known in the art. Preferably, the chimeric genes are carried in an expression vector. Each chimeric gene can be included in a separate expression vector. Alternatively, the two chimeric genes encoding for the two fusion proteins required in the two-hybrid system of the present invention can be included in the same expression vector. The chimeric genes may have a constitutive promoter to allow constitutive expression of the chimeric genes to produce the fusion proteins. Inducible or repressible promoters may also be used such that the expression of the fusion proteins can be easily controlled. Also, the expression vectors carrying one or more chimeric genes can be maintained in the yeast haploid cell as self-replicating extra-chromosomal elements or stably integrated into a host chromosome.

When a transcriptional activation domain and a DNA-binding domain are used as the effectors in the fusion proteins, they may be derived from various known transcriptional activators, e.g., GAL4, GCN4, ARD1, ACE1, the human estrogen receptor, *E. coli* LexA protein, herpes simplex virus VP16 (Triezenberg et al., *Genes Dev.* 2:718–729 (1988)), the *E. coli* B42 protein (acid blob, see Gyuris et al., *Cell*, 75:791–803 (1993)), NF-kappaB p65, and the like.

When a transcriptional repressor domain (TRD) is used as an effector polypepitde in a fusion protein, the repressor domain can be selected from a variety of transcriptional repressors known in the art including, e.g., the Kruppel protein, the engrailed protein, the knirps protein, the paired protein and the even-skipped protein, all from Drosophila; the SIN3, GAL80, and TUP1 proteins, all from *Saccharomyces cerevisiae*; the tet repressor; the Egr-1, WT1, RARa, KRAB, verbA, YY1, ADE1B, E4B4, SCIP, kid-1, Znf2, and kox-1 proteins; and the like. Such repressor proteins can also be used in embodiments such as those in FIGS. 2E, 3C, 3D, 4C, 4D, and 4F.

Since the transcriptional activation domain and DNA binding domain are separable in many transcriptional activators, the transcriptional activation domain (AD) and DNA binding domain (AD) in a pair of fusion proteins may be derived from the same transcriptional activator or different transcriptional activators. Likewise, the transcriptional repressor domain (RD) and DNA binding domain (AD) in a pair of fusion proteins may also be from the same or different transcriptional repressors. Similarly, the transcriptional activators and repressors in the embodiments such as those in FIGS. 2D, 2E, 3C, 3D, 4C, 4D, 4F and 4G can be hybrid proteins with their DNA binding domains and activation domains (repressor domains) being from different proteins.

To provide a reporter gene in a test yeast haploid cell encoding a functional MAT-alpha1p or MAT-alpha2p protein and having a promoter comprising an inducible or repressor element, the native promoter of the endogenous MAT-alpha1 or MAT-alpha2 gene can be modified or replaced by genetic engineering methods, e.g., homologous recombination. Preferably, an exogenous reporter gene may be introduced into the yeast haploid cell. The exogenous reporter gene may be carried in a suitable expression vector, which is introduced into the yeast haploid cell by any methods known in the art. Once the expression vector is introduced into the host cell, the expression vector can be maintained as an extra-chromosomal entity in the cell. Alternatively, suitable elements (e.g., those for homologous recombination) can be included into the expression vector to facilitate the integration of the exogenous reporter gene into a chromosome of the host yeast haploid cell.

The expression of recombinant proteins in yeasts is a well developed area, and the techniques useful in this respect are disclosed in detail in *The Molecular Biology of the Yeast Saccharomyces*, Eds. Strathern et al., Vols. I and II, Cold Spring Harbor Press, 1982; Ausubel et al., *Current Protocols in Molecular Biology*, New York, Wiley, 1994; and Guthrie and Fink, *Guide to Yeast Genetics and Molecular Biology*, in *Methods in Enzymology*, Vol. 194, 1991, all of which are incorporated herein by reference. Sudbery, *Curr. Opin. Biotech.*, 7:517–524 (1996) reviews the success in the art in expressing recombinant proteins in various yeast species; the entire content and references cited therein are incorporated herein by reference. In addition, Bartel and Fields, eds., *The Yeast Two-Hybrid System*, Oxford University Press, New York, N.Y., 1997 contains extensive discussions of recombinant expression of fusion proteins in yeasts in connection with various yeast two-hybrid systems, and cites numerous relevant references. These and other methods known in the art can all be used for purposes of the present invention. The application of such methods to the present invention should be apparent to a skilled artisan apprised of the present disclosure.

Generally, the vectors for recombinant expression in yeast include a yeast replication origin such as the 2µ origin or the ARSH4 sequence for the replication and maintenance of the vectors in yeast cells. Preferably, the vectors also have a bacteria origin of replication (e.g., ColE1) and a bacteria selection marker (e.g., amp$^R$ marker, i.e., bla gene). Optionally, the CEN6 centromeric sequence is included to control the replication of the vectors in yeast cells.

Any constitutive or inducible promoters capable of driving gene transcription in yeast cells may be employed to control the expression of the chimeric genes. Such promoters are operably linked to the coding region of the chimeric genes. Examples of suitable constitutive promoters include, but are not limited to, the yeast ADH1, PGK1, TEF2, GPD1, HIS3, and CYC1 promoters. Examples of suitable inducible promoters include but are not limited to the yeast GAL1 (inducible by galactose), CUP1 (inducible by $Cu^{++}$), MEL1 (inducible by galactose), FUS1 (inducible by pheromone) promoters; the AOX/MOX promoter from *H. polymorpha* and *P. Pastoris* (repressed by glucose or ethanol and induced by methanol); chimeric promoters such as those that contain LexA operators (inducible by LexA-containing transcription factors); and the like. Inducible promoters are preferred when the fusion proteins encoded by the chimeric genes are potentially toxic to the host cells.

For purposes of transcriptional activation or repression of the reporter gene expression, suitable transcription activators include, but are not limited to, GAL4, GCN4, ARD1, the human estrogen receptor, *E. coli* LexA protein, herpes simplex virus VP16 (Triezenberg et al., *Genes Dev.* 2:718–729 (1988)), the *E. coli* B42 protein (acid blob, see Gyuris et al., *Cell*, 75:791–803 (1993)), NF-kappaB p65, and the like. In addition, hybrid transcriptional activators composed of a DNA binding domain from one transcriptional activator and an activation domain from another transcriptional activator are also useful. Examples of transcription suppressors include the Kruppel protein, the engrailed protein, the knirps protein, the paired protein and the even-skipped protein, all from Drosophila; the SIN3, GAL80, and TUP1 proteins, all from *Saccharomyces cerevisiae*; the tet repressor; the Egr-1, WT1, RARa, KRAB, verbA, YY1, ADE1B, E4B4, SCIP, kid-1, Znf2, and kox-1 proteins; and the like.

As discussed above, in the various embodiments of the present invention, the reporter gene contains a promoter responsive to a transcriptional activator (or repressor) reconstituted from the DNA binding domain and transcriptional activation domain (or transcriptional repressor domain) in the fusion proteins, or responsive to a transcriptional activator or repressor released from the ubiquitin-based fusion proteins. Any transcriptional elements known in the art may be used so long as they confer on the reporter gene the ability to respond to a transcriptional activator or repressor reconstituted or released as a result of the interaction between two test polypeptides in the fusion proteins expressed in the test haploid cell. For example, the transcriptional elements specifically interacting with the transcriptional activators or repressors described above are well known in the art. See.e.g., Hanna-Rose and Hansen, *Trends. Genet.*, 12:229–234 (1996). In a preferred embodiment, the reporter gene is under the control of the GAL1–10 promoter and the two fusion proteins contain the GAL4 DNA binding domain and GAL4 activation domain, respectively as effector polypeptides.

If it is desirable, certain transcription repressing sequences such as the upstream repressing sequence (URS) from SPO13 promoter can be operably linked to the promoter sequence, e.g., linked to the 5' end of the promoter region. Such upstream repressing sequences function to fine-tune the expression level of the chimeric genes or the reporter genes.

Preferably, a transcriptional termination signal is operably linked to the chimeric genes or the reporter genes in the vectors. Generally, transcriptional termination signal sequences derived from, e.g., the CYC1 and ADH1 genes can be used.

Termination sequences such as the polyadenylation signals derived from bovine growth hormone gene, SV40, lacZ and AcMNPV polyhedral genes may also be operably linked to the chimeric genes. In addition, an epitope tag coding sequence for detection and/or purification of the fusion proteins can also be incorporated into the expression vectors. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies to many epitope tags are generally commercially available. In addition, nucleic acid sequences encoding nuclear localization signals may also be included in a chimeric gene if it is desirable for the fusion protein encoded by the chimeric gene to be localized in cell nucleus.

Additionally, it is preferred that the expression vectors contain one or more selecting markers for the selection and maintenance of only those test haploid yeast cells that harbor the chimeric genes and/or reporter genes and optionally, relay genes of the present invention. Any selectable markers known in the art can be used for purposes of this invention so long as yeast cells expressing the chimeric gene(s) and/or reporter genes of the present invention can be positively identified or negatively selected. Examples of markers that can be positively identified are those based on color assays, including the lacZ gene which encodes β-galactosidase, the firefly luciferase gene, secreted alkaline phosphatase, horseradish peroxidase, the blue fluorescent protein (BFP), and the green fluorescent protein (GFP) gene (see Cubitt et al., *Trends Biochem. Sci.*, 20:448–455 (1995)). Other markers emitting fluorescence, chemiluminescence, UV absorption, infrared radiation, and the like can also be used. Among the markers that can be selected are auxotrophic markers that include, but are not limited to, URA3, HIS3, TRP1, LEU2, LYS2, ADE2, and the like. Typically, for purposes of auxotrophic selection, the yeast host cells transformed with bait vector and/or prey vector are cultured in a medium lacking a particular nutrient. Other selectable markers are not based on auxotrophies, but rather on resistance or sensitivity to an antibiotic or other xenobiotic. Examples include but are not limited to chloramphenicol acetyl transferase (CAT) gene, which confers resistance to chloramphenicol; CAN1 gene, which encodes an arginine permease and thereby renders cells sensitive to canavanine (see Sikorski et al., *Meth. Enzymol.*, 194:302–318 (1991)); the bacterial kanamycin resistance gene (kan$^R$), which renders eucaryotic cells resistant to the aminoglycoside G418 (see Wach et al., *Yeast*, 10: 1793–1808 (1994)); and CYH2 gene, which confers sensitivity to cycloheximide (see Sikorski et al., *Meth. Enzymol.*, 194:302–318 (1991)). In addition, the CUP1 gene, which encodes metallothionein and thereby confers resistance to copper, is also a suitable selection marker. Each of the above selection markers may be used alone or in combination. One or more selection markers can be included in a particular expression vector.

As will be apparent, the selection markers used should complement the haploid host strains in which the expression vectors are expressed. In other words, when a gene is used as a selection marker gene, a yeast strain lacking the selection marker gene (or having mutation in the corresponding gene) should be used as haploid host cells to make test yeast haploid cells.

In addition, since a test yeast haploid cell is to be examined for its ability to mate with a reporter yeast haploid cell to form a diploid cell, reporting markers should be included in the yeast test haploid cell and/or the reporter yeast haploid cell for purposes of detecting a mating event. In a preferred embodiment, a test yeast haploid cell has a first reporting marker and a reporter yeast haploid cell has a second reporting marker. The reporting markers should be designed such that mating between the test haploid cell and the reporter haploid cell can be detected. Preferably, the reporting markers are positively selectable genetic markers. Typically, the test haploid cell and the reporter haploid cell have different reporting markers. Any of the above-discussed selection markers for the expression vectors can be used as a reporting marker. However, it is preferred that, in a particular haploid cell, the reporting marker is different from any selection markers in the haploid cell.

In a preferred embodiment, auxotrophic markers such as URA3, HIS3, TRP1, LEU2, LYS2, ADE2 and the like are used. Thus, for example, the test haploid cell may be defective in its URA3 gene (Ura$^-$) and cannot grow in a medium lacking uracil. However, the test haploid cell has a functional HIS3 gene (His$^+$). The reporter haploid cell has a functional URA3 gene (Ura$^+$) but is defective in HIS3 (His$^-$) and cannot grow on a His$^-$ medium. Thus, on a medium lacking both histidine and uracil, neither haploid cell can grow. Only diploid cells resulting from mating between a test haploid cell and a reporter haploid cell can form colonies.

In another embodiment, antibiotics resistance is used as reporting markers. For example, a test haploid cell may have a chloramphenicol acetyl transferase (CAT) gene, which confers resistance to chloramphenicol, but does not express the bacterial kanamycin resistance gene (kan$^R$), which is required for resistance to the aminoglycoside G418. In contrast, a reporter haploid cell may express the kanamycin resistance gene but not the CAT gene. By co-culturing the two cells in a medium containing both chloramphenicol and G418 under conditions conducive to mating, the haploid cells will not grow and only a diploid cell resulting from mating can propagate.

Mating can be conducted in any known methods in the art. Test haploid cells can be mixed with reporter haploid cells in a liquid medium or on a solid medium (e.g., agar plate) to allow the test haploid cells to be in contact with the reporter haploid cells. Mating is preferably conducted in a relatively rich medium for a sufficient time, e.g., one hour to overnight. Selection pressure can be imposed on the yeast cells at the time of mating, but preferably after mating is completed. In the case of a screen assay using a reverse two-hybrid system of the present invention, the test haploid cells and reporter haploid cells should be contacted with each other in the presence of one or more test compounds.

The mating-based yeast two-hybrid system of the present invention is useful in detecting an interaction between two test polypeptides. Specifically, a scheme in which mating occurs only when two test polypeptides interact with each other is preferably employed. For example, the embodiments shown in FIGS. 2A, 2B, 2D, 3A, 3E, 4B, 4C, and 4D are especially suitable for such purposes.

Many protein interactions require the participation of other proteins. Thus, the mating-based system of the present invention can also be adapted to a multi-hybrid assay. See U.S. Pat. No. 5,695,941; Chang et al., *Cell*, 79:131–141

(1994); Tirode et al., *J. Biol. Chem.*, 272:22995–22999 (1997); Van Criekinge et al., *Anal. Biochem.*, 263:62–66 (1998); and Pause et al., *Proc. Natl. Acad. Sci. USA*, 96:9533–9538 (1999), all of which are incorporated herein by reference. Accordingly, genes encoding proteins other than those in the fusion proteins can be co-expressed in a yeast test haploid cell with the chimeric genes and reporter genes as described above. Such additional genes may be incorporated into one of the expression vectors or the reporting vector. Alternatively, they can be expressed in separate vectors under control of a constitutive or inducible promoter.

In a specific embodiment, the additional test proteins are enzymes capable of post-translationally modifying at least one of the test polypeptides in the fusion proteins. This is especially useful when one or both of the test polypeptides are believed to contain consensus sequences for certain modifying enzymes. A two-hybrid system involving modifying enzymes has been disclosed in, e.g., U.S. Pat. No. 5,637,463, which is incorporated herein by reference. This system can be applied to the present invention upon appropriate modifications as will be apparent to a skilled artisan apprised of the present disclosure. Examples of useful modifying enzymes include protein kinases, which catalyze protein phosphorylation (e.g., serine/threonine phosphorylation, tyrosine phosphorylation by tyrosine kinase, see Lioubin et al., *Genes Dev.*, 10: 1084–1095 (1996); Keegan et al., *Oncogene*, 12:1537–1544 (1996)), and enzymes that catalyze fatty acid acylation, ADP-ribosylation, myristylation, and glycosylation. It is recognized that over-expression of certain modifying enzymes such as tyrosine kinases may be toxic to host cells. This can be avoided by using inducible promoters or weak promoters to drive the expression of the toxic modifying enzymes in host cells.

In accordance with another aspect of the present invention, the mating-based two-hybrid system is used for selecting a compound capable of modulating an interaction between interacting proteins. By "modulating" or "modulation" it is intended to mean that a compound interferes with, weakens, dissociates or disrupts particular protein-protein interactions, or alternatively, initiates, facilitates or stabilizes particular protein-protein interactions.

As is now known in the art, most proteins exert their cellular functions through their interactions with other proteins. Protein-protein interactions form the basis of almost all biological processes. Each biological process or cell machine is composed of a network of interacting proteins. For example, many enzymatic reactions are associated with large protein complexes formed by interactions among enzymes, protein substrates and protein modulators. In addition, protein-protein interactions are also part of the mechanism for signal transduction and other basic cellular functions such as cell cycle regulation, gene transcription, and translation. Undoubtedly, protein-protein interactions are involved in various disease pathways. Thus, compounds that modulate particular protein-protein interactions in disease pathways are potential therapeutic agents useful in treating or preventing diseases. In this respect, both compounds capable of interfering with undesirable protein-protein interactions and compounds that trigger or stabilize desirable protein-protein interactions can be useful.

The mating-based system of the present invention is especially suited for screening such compounds. Thus, two proteins whose interaction needs be modulated are used as test polypeptides in the fusion proteins to be expressed in a test yeast haploid cell. The test haploid cell is contacted with a suitable reporter haploid cell under conditions conducive to mating and in the presence of a test compound. The ability of the test compound to modulate the interaction between the two test polypeptides is determined by detecting the presence or absence of diploid cells resulted from mating.

Any test compounds may be screened in the screen assays of the present invention to select modulators of a protein-protein interaction. By the term "selecting" or "select" modulators it is intended to encompass both (a) choosing compounds from a group of compounds previously unknown to be modulators of a particular protein-protein interaction, and (b) testing compounds that are known to be capable of modulating a particular protein-protein interaction. Both types of compounds are generally referred to herein as "test compounds." The test compounds may include, by way of example, proteins (e.g., antibodies, small peptides, artificial or natural proteins), nucleic acids, and derivatives, mimetics and analogs thereof, and small organic molecules having a molecular weight of no greater than 10,000 dalton, more preferably less than 5,000 dalton. For example, combinatorial technologies can be employed to construct combinatorial libraries of small organic molecules or small peptides. See generally, e.g., Kenan et al., *Trends Biochem. Sc.*, 19:57–64 (1994); Gallop et al.,*J. Med. Chem.*, 37:1233–1251 (1994); Gordon et al., *J. Med. Chem.*, 37:1385–1401 (1994); Ecker et al., *Biotechnology*, 13:351–360 (1995). Such combinatorial libraries of compounds can be applied to the screen assays of the present invention to identify specific modulators of a particular protein-protein interaction. In the case of random peptide libraries, the random peptides can be co-expressed with the fusion proteins of the present invention in test yeast haploid cells. See e.g., Yang et al., *Nucl. Acids Res.*, 23:1152–1156 (1995). Alternatively they can be added to the yeast culture medium for uptake. Random peptides can be provided in, e.g., recombinantly expressed libraries (e.g., phage display libraries), or in vitro translation-based libraries (e.g., mRNA display libraries, see Wilson et al., *Proc Natl Acad Sci* 98:3750–3755 (2001)).

The screen assay of the present invention can be used to select compounds capable of triggering or stabilizing particular protein-protein interactions. As is known in the art, many protein-protein interactions require the presence of small molecule ligands or other proteins. For example, immune suppressants such as cyclosporin A (CsA), FK506, and rapamycin are known to exert their therapeutic effect by mediating the binding of immunophilins to specific target proteins. Thus, two proteins whose interaction needs be initiated or strengthened by a therapeutic compound are used as test polypeptides in the fusion proteins expressed in a test yeast haploid cell. The fusion proteins are allowed to interact with each other in the presence of one or more test compounds. The test haploid cell is contacted with a suitable reporter haploid cell under conditions conducive to mating and in the presence of the test compound(s). A scheme is preferred in which mating occurs only when the two test polypeptides interact with each other. Examples of such schemes include those described in FIGS. 2A, 2B, 2D, 3A, 3E, 4B, 4C, and 4D. The ability of the test compound(s) to initiate or strengthen the interaction between the two test polypeptides is determined by detecting the presence of diploid cells resulted from mating.

The screen assay of the present invention is particularly useful in identifying compounds capable of interfering with or disrupting a particular protein-protein interaction. For example, compounds capable of dissociating interactions between oncogene products and their cellular targets are potential anti-cancer agents. Preferably, a reverse two-hybrid assay is used. That is, a scheme is preferred in which mating occurs in the absence of an interaction between the two test polypeptides. Examples of such schemes include those described in FIGS. 1B, 1C, 2E, 3B, 3C, 3D, 4A, and 4E–G. Again, two proteins of interest whose interaction needs be disrupted are used as test polypeptides in the mating-based two-hybrid system of the present invention. The fusion proteins are expressed and allowed to interact with each other in the presence of one or more test compounds. The test haploid cell expressing the fusion proteins is contacted with a suitable reporter haploid cell under conditions conducive to mating and in the presence of the test compound(s). The ability of the test compound(s) to interfere with or disrupt the interaction between the two test polypeptides is determined by detecting the presence of diploid cells resulted from mating.

The screen assays of the present invention for identifying compounds capable of modulating protein-protein interactions can also be fine-tuned by various techniques to adjust the thresholds or sensitivity of the positive and negative selections. The uptake of test compounds by the test haploid cells can be adjusted. For example, yeast high uptake mutants such as the erg6 mutant strains can facilitate yeast uptake of the test compounds. See Gaber et al., $Mol.\ Cell.\ Biol.$, 9:3447–3456 (1989). The methods for modifying yeast permeability disclosed in U.S. Pat. No. 5,821,038 can also be used, which is incorporated herein by reference. Essentially, two or more genes controlling cellular permeability of yeast at different levels are modified. Examples of such genes include XRE, KTR, MN, CSD, CHS, OCH, SKN1, PMR1, PMT1, ERD1, VGR1, VGR4, CAL3, SHC1, DHS1, SRB1, PKC1, BCK1, MKK1, MKK2, MPK1, PPZ1, PPZ2, PMI1, BGL2, ERG10, ERG11, ERG13, RMG1, RMG2, ERG12, ERG8, ERG19, IDI1, ERG20, ERG9, ERG1, ERG18, ERG7, ERG17, ERG16, ERG24, ERG6, ERG2, ERG3, ERG5, ERG4, SNQ1, SNQ2, SNQ3, STE6, PDR1, PDR2, PDR3, PDR4, PDR6, PDR7, PDR9 and PDR11. See U.S. Pat. No. 5,821,038. In addition, the test yeast haploid cell may also be treated with chemicals such as polymixin B nonapeptide to increase permeability.

Additionally, where the production of MAT-alpha1p or MAT-alpha2p protein is dependent upon an interaction between two test polypeptides, the basal level of MAT-alpha1 or MAT-alpha2 reporter gene expression may be reduced. For this purpose, a DNA fragment encoding the 5' untranslated region of yeast GCN4 mRNA can be inserted into the reporter gene between the promoter and the coding sequence. Various mRNA species bearing the GCN4 5' UTR are poorly translated under normal growth conditions, yet their translation can be stimulated by exogenous 3-aminotriazole. Thus, the insertion of the GCN4 5' UTR may lead to acceptably low reporter gene expression levels, and 3-aminotriazole may be used to titrate the reporter gene expression to a level such that an interaction between two test polypeptides can lead to changes in mating behavior.

Additionally, if necessary, some of the a- or alpha-specific genes can be placed under control of a constitutive promoter that is not regulated by MAT-alpha1p or MAT-alpha2p. For example, it is possible that members of the MAT-alpha2p-regulated mating genes (e.g., MFa1, MFa2, STE2, STE6, and BAR1) are differentially sensitive to MAT-alpha2p levels. Likewise, the alpha-specific genes may respond to a MAT-alpha1p level differently. By constitutively expressing at high levels those mating-type specific gene products that are least sensitive to MAT-alpha1- or MAT-alpha2-stimulated expression, mating behavior can be made directly dependent on those genes most highly controlled by MAT-alpha1 or MAT-alpha2. Such maneuvers can ensure that the mating phenotype of the tester strain is sensitive to and dependent on protein-protein interactions between the two test polypeptides.

Once test compounds are selected capable of modulating the interaction between two test polypeptides, a data set including data defining the identity or characteristics of the test compounds can be generated. The data set may include information relating to the properties of a selected test compound, e.g., chemical structure, chirality, molecular weight, melting point, etc. Alternatively, the data set may simply include assigned identification numbers understood by the researchers conducting the screening assay and/or researchers receiving the data set as representing specific test compounds. The data or information can be cast in a transmittable form that can be communicated or transmitted to other researchers, particularly researchers in a different country. Such a transmittable form can vary and can be tangible or intangible. For example, the data set defining one or more selected test compounds can be embodied in texts, tables, diagrams, molecular structures, photographs, charts, images or any other visual forms. The data or information can be recorded on a tangible media such as paper or embodied in computer-readable forms (e.g., electronic, electromagnetic, optical or other signals). The data in a computer-readable form can be stored in a computer usable storage medium (e.g., floppy disks, magnetic tapes, optical disks, and the like) or transmitted directly through a communication infrastructure. In particular, the data embodied in electronic signals can be transmitted in the form of email or posted on a website on the Internet or Intranet. In addition, the information or data on a selected test compound can also be recorded in an audio form and transmitted through any suitable media, e.g., analog or digital cable lines, fiber optic cables, etc., via telephone, facsimile, wireless mobile phone, Internet phone and the like.

Thus, the information and data on a test compound selected in a screening assay described above or by virtual screening as discussed below can be produced anywhere in the world and transmitted to a different location. For example, when a screening assay is conducted offshore, the information and data on a selected test compound can be generated and cast in a transmittable form as described above. The data and information in a transmittable form thus can be imported into the U.S. or transmitted to any other countries, where the data and information may be used in further testing the selected test compound and/or in modifying and optimizing the selected test compound to develop lead compounds for testing in clinical trials.

Once an effective compound is identified, structural analogs or mimetics thereof can be produced based on rational drug design with the aim of improving drug efficacy and stability, and reducing side effects. Methods known in the art for rational drug design can be used in the present invention. See, e.g., Hodgson et al., $Bio/Technology$, 9:19–21 (1991); U.S. Pat. Nos. 5,800,998 and 5,891,628, all of which are incorporated herein by reference. An example of rational drug design is the development of HIV protease inhibitors. See Erickson et al., $Science$, 249:527–533 (1990).

Preferably, structural information on the protein-protein interaction to be modulated is obtained. For example, each of the interacting pair can be expressed and purified. The purified interacting protein pairs are then allowed to interact with each other in vitro under appropriate conditions. Optionally, the interacting protein complex can be stabilized by crosslinking or other techniques. The interacting complex can be studied using various biophysics techniques including, e.g., X-ray crystallography, NMR, computer modeling, mass spectrometry, and the like. Likewise, structural information can also be obtained from protein complexes formed by interacting proteins and a compound that initiates or stabilizes the interaction of the proteins.

In addition, understanding of the interaction between the proteins of interest in the presence or absence of a modulating compound can also be derived from mutagenesis analysis using the above-described detection method of the present invention. Indeed, the detection method of this invention is particularly useful in analyzing and characterizing protein-protein interactions. In this respect, various mutations can be introduced into the interacting proteins and the effect of the mutations on protein-protein interaction is examined by the above-discussed detection method.

Various mutations including amino acid substitutions, deletions and insertions can be introduced into a protein sequence using conventional recombinant DNA technologies. Generally, it is particularly desirable to decipher the protein binding sites. Thus, it is important that the mutations introduced only affect protein-protein interaction and cause minimal structural disturbances. Mutations are preferably designed based on knowledge of the three-dimensional structure of the interacting proteins. Preferably, mutations are introduced to alter charged amino acids or hydrophobic amino acids exposed on the surface of the proteins, since ionic interactions and hydrophobic interactions are often involved in protein-protein interactions. Alternatively, the "alanine scanning mutagenesis" technique is used. See Wells, et al., *Methods Enzymol.*, 202:301–306 (1991); Bass et al., *Proc. Natl. Acad. Sci. USA*, 88:4498–4502 (1991); Bennet et al., *J. Biol. Chem.*, 266:5191–5201 (1991); Diamond et al., *J. Virol.*, 68:863–876 (1994). Using this technique, charged or hydrophobic amino acid residues of the interacting proteins are replaced by alanine, and the effect on the interaction between the proteins is analyzed using the above-described detection method. For example, the entire protein sequence can be scanned in a window of five amino acids. When two or more charged or hydrophobic amino acids appear in a window, the charged or hydrophobic amino acids are changed to alanine using standard recombinant DNA techniques. The thus mutated proteins are used as "test proteins" in the above-described detection method to examine the effect of the mutations on protein-protein interaction. Preferably, the mutagenesis analysis is conducted both in the presence and in the absence of an identified modulating compound. In this manner, the domains or residues of the proteins important to protein-protein interaction and/or the interaction between the modulating compound and the proteins can be identified.

Based on the structural information obtained, structural relationships between the interacting proteins as well as between the identified compound and the interacting proteins are elucidated. The moieties and the three-dimensional structure of the identified compound, i.e., lead compound, critical to its modulating effect on the interaction of the known proteins of interest are revealed. Medicinal chemists can then design analog compounds having similar moieties and structures.

In addition, an identified peptide compound capable of modulating particular protein-protein interactions can also be analyzed by the alanine scanning technique to determine the domains or residues of the peptide important to its modulating effect on particular protein-protein interactions. The peptide compound can be used as a lead molecule for rational design of small organic molecules. See Huber et al., *Curr. Med. Chem.*, 1:13–34 (1994).

The residues or domains critical to the modulating effect of the identified compound constitute the active region of the compound known as its "pharmacophore." Once the pharmacophore has been elucidated, a structural model can be established by a modeling process that may incorporate data from NMR analysis, X-ray diffraction data, alanine scanning, spectroscopic techniques and the like. Various techniques including computational analysis, similarity mapping and the like can all be used in this modeling process. See e.g., Perry et al., in *OSAR: Quantitative Structure-Activity Relationships in Drug Design*, pp.189–193, Alan R. Liss, Inc., 1989; Rotivinen et al., *Acta Pharmaceutical Fennica*, 97:159–166 (1988); Lewis et al., *Proc. R. Soc. Lond.*, 236:125140 (1989); McKinaly et al., *Annu. Rev. Pharmacol. Toxiciol.*, 29:111–122 (1989). Commercial molecular modeling systems available from Polygen Corporation, Waltham, Mass., include the CHARMm program, which performs the energy minimization and molecular dynamics functions, and QUANTA program which performs the construction, graphic modeling and analysis of molecular structure. Such programs allow interactive construction, visualization and modification of molecules. Other computer modeling programs are also available from BioDesign, Inc. (Pasadena, Calif.), Hypercube, Inc. (Cambridge, Ontario), and Allelix, Inc. (Mississauga, Ontario, Canada).

A template can be formed based on the established model. Various compounds can then be designed by linking various chemical groups or moieties to the template. Various moieties of the template can also be replaced. In addition, in the case of a peptide lead compound, the peptide or mimetics thereof can be cyclized, e.g., by linking the N-terminus and C-terminus together, to increase its stability. These rationally designed compounds are further tested. In this manner, pharmacologically acceptable and stable compounds with improved efficacy and reduced side effect can be developed. The compounds identified in accordance with the present invention can be incorporated into a pharmaceutical formulation suitable for administration to an individual.

The present invention also encompasses the various test yeast haploid cells described above. In addition, various test yeast haploid precursor cells for making the test yeast haploid cells also fall within the scope of the present invention. Such precursor cells can be used in making test yeast haploid cells. For example, a test yeast haploid precursor cell is provided which expresses a functional MAT-alpha2p protein. In addition, the test yeast haploid precursor cell has a MAT-alpha1 gene whose expression is under the control of an inducible promoter such that the transcription of the gene occurs only in the presence of a particular transcriptional activator. Examples of such a transcriptional activator include, e.g., GAL4, GCN4, ARD1, the human estrogen receptor, *E. coli* LexA protein, herpes simplex virus VP16 (Triezenberg et al., *Genes Dev.* 2:718–729 (1988)), the *E. coli* B42 protein (acid blob, see Gyuris et al., *Cell*, 75:791–803 (1993)), NF-kappaB p65, and the like. In addition to naturally occurring transcriptional activators, hybrid transcriptional activators composed of a DNA binding domain from one transcriptional activator and an activation domain from another transcriptional activator are also useful. Also contemplated are reconstituted transcriptional activators formed by two fusion proteins one containing a DNA-binding domain and a transcriptional activation domain, respectively. Such a test yeast haploid precursor cell can be prepared by genetically engineering an alpha cell. For example, the native promoter for the MAT-alpha1 gene can be replaced with a promoter having an inducible element responsive to any of the above transcriptional activators.

In another embodiment, a test yeast haploid precursor cell expresses a functional MAT-alpha2p protein. In addition, the test yeast haploid cell has a MAT-alpha1 gene whose expression is under the control of a promoter having a repressor element such that the gene is expressed constitutively in the absence of a transcriptional repressor corresponding to the repressor element, and repressed in the presence of the transcriptional repressor. Any of the above-described transcriptional repressors can be used. In addition to naturally occurring transcriptional repressors, hybrid transcriptional repressors composed of a DNA binding domain from one transcriptional repressor and a repressor domain from another transcriptional repressor are also useful. Also contemplated are reconstituted transcriptional repressors formed by two fusion proteins one containing a DNA-binding domain and a transcriptional repressor domain, respectively. Such a test yeast haploid precursor cell can be prepared by genetically engineering an alpha cell. For example, the native promoter for the MAT-alpha1 gene can be replaced with a promoter having a repressor element responsive to any of the above transcriptional repressors.

In yet another embodiment, the test yeast haploid precursor cell does not express a functional MAT-alpha1p protein. That is, it has a mat-alpha1$^-$ genotype. In addition, the cell has a MAT-alpha2 gene whose expression is under the control of an inducible promoter such that the transcription of the gene occurs only in the presence of a particular transcriptional activator. Examples of such a transcriptional activator include, e.g., GAL4, GCN4, ARD1, the human estrogen receptor, $E.$ $coli$ LexA protein, herpes simplex virus VP16 (Triezenberg et al., $Genes$ $Dev.$ 2:718–729 (1988)), the $E.$ $coli$ B42 protein (acid blob, see Gyuris et al., $Cell$, 75:791–803 (1993)), NF-kappaB p65, and the like. In addition to naturally occurring transcriptional activators, hybrid transcriptional activators composed of a DNA binding domain from one transcriptional activator and an activation domain from another transcriptional activator are also useful. Also contemplated are reconstituted transcriptional activators formed by two fusion proteins one containing a DNA-binding domain and a transcriptional activation domain, respectively. Such a test yeast haploid precursor cell can be prepared by genetically engineering an alpha cell. For example, the endogenous MAT-alpha1 gene of an alpha cell can be knocked out and the native promoter for the MAT-alpha2 gene can be replaced with a promoter having an inducible element responsive to any of the above transcriptional activators. Alternatively, the endogenous MAT-alpha2 gene is also knocked out and an exogenous reporter gene is introduced. The reporter gene encodes a functional MAT-alpha2p protein and has an inducible promoter.

The present invention also provides a test yeast haploid precursor cell which lacks a functional MAT-alpha1p protein and the expression of functional MAT-alpha2p protein is under the control of a promoter having a repressor element such that the gene is expressed constitutively in the absence of a transcriptional repressor corresponding to the repressor element, and repressed in the presence of the transcriptional repressor. Any of the above-described transcriptional repressors can be used. In addition to naturally occurring transcriptional repressors, hybrid transcriptional repressors composed of a DNA binding domain from one transcriptional repressor and a repressor domain from another transcriptional repressor are also useful. Also contemplated are reconstituted transcriptional repressors formed by two fusion proteins one containing a DNA-binding domain and a transcriptional repressor domain, respectively. Such a test yeast haploid precursor cell can be prepared by genetically engineering an alpha cell. For example, the endogenous MAT-alpha1 gene of an alpha cell can be knocked out and the native promoter for the MAT-alpha2 gene can be replaced with a promoter having a repressor element responsive to any of the above transcriptional repressors. Alternatively, the endogenous MAT-alpha2 gene is also knocked out and an exogenous reporter gene is introduced. The reporter gene encodes a functional MAT-alpha2p protein and has a promoter comprising a repressor element.

Preferably, the test yeast haploid precursor cells have a reporting marker as described above. In addition, in preferred embodiments of the test yeast haploid precursor cells, other transcriptional or translational control elements may also be included in the promoter or between the promoter and the coding sequence in the reporter genes. For example, a DNA fragment encoding the 5' untranslated region of yeast GCN4 mRNA can be inserted into the reporter gene between the promoter and the coding sequence of a reporter gene. In another example, the upstream repressing sequence (URS) from SPO13 promoter can be operably linked to the promoter of a reporter gene.

In accordance with another aspect of the present invention, a kit is provided for preparing the test yeast haploid cells of the present invention and/or for practicing the above-described methods for detecting protein-protein interactions. In particular, the kit can be used in detecting and/or characterizing protein-protein interactions, and in screen assays for identifying specific compounds capable of modulating known protein-protein interactions. Accordingly, components that can be included in the kit will be apparent to a skilled artisan apprised of the present disclosure. Specifically, the test yeast haploid cells, test yeast haploid precursor cells, expression vectors containing a chimeric gene encoding fusion proteins, expression vectors carrying a reporter gene or a relay gene, and reporter haploid cells provided according to the various embodiments of the present invention can be included in a kit. Typically, the various components of the kit are placed in a rack, compartmentalized support or carrier, or enclosed container for purposes of organizing and/or transporting the kit. Preferably the kit also includes instructions for using the kit to practice the present invention.

In one embodiment, the kit includes a test yeast haploid precursor cell of the present invention and at least a pair of expression vectors. One expression vector contains a DNA sequence encoding a DNA-binding domain. The expression vector is constructed such that a DNA sequence encoding a test polypeptide can be conveniently inserted into the expression vector to form a chimeric gene encoding a fusion protein having the DNA-binding domain and the test polypeptide. Preferably, the expression vector comprises a restriction enzyme recognition site, preferably a multiple cloning site (MCS) operably linked to the DNA sequence encoding the DNA-binding domain such that a DNA sequence encoding a test polypeptide of interest can be conveniently inserted in frame into the MCS and a fusion protein can be produced containing the DNA-binding domain and the test polypeptide. The other expression vector in the kit includes a DNA sequence encoding a transcriptional activation domain or transcriptional repressor domain. Preferably, a restriction enzyme recognition site, or more preferably a multiple cloning site (MCS) is operably linked to the DNA sequence encoding the transcriptional activation domain or transcriptional repressor domain. Thus, a DNA sequence encoding another test polypeptide of interest can be conveniently inserted in frame into the MCS and a fusion protein can be produced containing the transcriptional activation domain (or transcriptional repressor domain) and the test polypeptide. In a preferred specific embodiment, the test yeast haploid precursor cell in the kit has a MAT-alpha1⁻ genotype. In addition, the production of the MAT-alpha2p protein in the cell is under the control of an inducible promoter having a recognition site for the DNA binding domain encoded by one of the two expression vectors in the kit. Preferably, the kit further includes a reporter yeast haploid cell of alpha-mating type. More preferably, the test yeast haploid cell precursor cell has a reporting marker that is different from a reporting marker of the reporter yeast haploid cell.

In another embodiment, the kit includes a test yeast haploid precursor cell of the present invention and at least a pair of expression vectors. One expression vector contains a DNA sequence encoding an N-terminal subdomain of ubiquitin or a modified form thereof. The expression vector is constructed such that a DNA sequence encoding a test polypeptide can be conveniently inserted into the expression vector to form a chimeric gene encoding a fusion protein having the test polypeptide and an N-terminal subdomain of ubiquitin or a modified form thereof. Preferably, the expression vector comprises a restriction enzyme recognition site, preferably multiple cloning site (MCS) operably linked to the DNA sequence encoding the N-terminal subdomain of ubiquitin or a modified form thereof such that a DNA sequence encoding a test polypeptide of interest can be conveniently inserted in frame into the MCS and a fusion protein can be produced containing the test polypeptide and the N-terminal subdomain of ubiquitin or a modified form thereof. The kit also includes another expression vector which contains a chimeric gene encoding a fusion protein having a C-terminal subdomain of ubiquitin or a modified form thereof fused at its C-terminus to a transcriptional activator or repressor. The expression vector is design such that a DNA sequence encoding a test polypeptide can be conveniently inserted into the expression vector such that a fusion protein is expressed having a C-terminal subdomain of ubiquitin linked at its N-terminus to another test polypeptide and at its C-terminus to the transcriptional repressor. Preferably, the expression vector has a restriction enzyme recognition site, preferably a multiple cloning site (MCS) operably linked to the 5' end of the chimeric gene that encodes a fusion protein having a C-terminal subdomain of ubiquitin or a modified form thereof fused at its C-terminus to a transcriptional activator or repressor.

In another embodiment, the kit contains at least an expression vector. Optionally, the kit also includes a test yeast haploid precursor cell. Preferably, the test yeast haploid precursor cell lacks a functional MAT-alpha1p protein and a functional MAT-alpha2p protein. The expression vector contains DNA sequences encoding N-intein or C-intein. See commonly assigned co-pending U.S. patent application Ser. No. 10/040,910, which is incorporated herein by reference. Thus, the expression vector may contain an expression cassette, which includes a first DNA sequence encoding an N-terminal portion of MAT-alpha2p. The first DNA sequence is operably linked to a second DNA sequence encoding an N-intein. In addition, the expression vector comprises a restriction enzyme recognition site, preferably multiple cloning site (MCS) operably linked to the second DNA sequence encoding the N-intein such that a DNA sequence encoding a first test polypeptide of interest can be conveniently inserted in frame into the MCS and a fusion protein can be produced containing the N-intein, the N-terminal portion of MAT-alpha2p and the test polypeptide fused. Preferably, in the fusion protein, the N-intein is linked to the C-terminus of the N-terminal portion of MAT-alpha2p, and the test polypeptide is fused to the C-terminus of the N-intein.

Preferably, the kit also includes a second expression vector containing an expression cassette. The expression cassette includes a first DNA sequence encoding a C-terminal portion of MAT-alpha2p. The first DNA sequence is operably linked to a second DNA sequence encoding a C-intein. In addition, the expression vector comprises a restriction enzyme recognition site, preferably multiple cloning site (MCS) operably linked to the second DNA sequence encoding the C-intein such that a DNA fragment encoding a second test polypeptide of interest can be conveniently inserted in frame into the MCS and a fusion protein can be produced containing the C-intein, the C-terminal portion of MAT-alpha2p and the second test polypeptide. Preferably, in the fusion protein, the C-intein is linked to the N-terminus of the C-terminal portion of MAT-alpha2p and the test polypeptide is fused to the N-terminus of the C-intein. Thus, upon intein-mediated protein splicing, the N-terminal and C-terminal portion of MAT-alpha2p can ligate and combine into a functional MAT-alpha2p protein.

In another embodiment, the kit includes one or more of the following expression vectors. One expression vector may contain an expression cassette, which includes a first DNA sequence encoding an N-terminal portion of a transcriptional activator or repressor. The first DNA sequence is operably linked to a second DNA sequence encoding an N-intein. In addition, the expression vector comprises a restriction enzyme recognition site, preferably multiple cloning site (MCS) operably linked to the second DNA sequence encoding the N-intein such that a DNA sequence encoding a first test polypeptide of interest can be conveniently inserted in frame into the MCS and a fusion protein can be produced containing the N-intein, the N-terminal portion of the transcriptional activator or repressor and the test polypeptide. Preferably, in the fusion protein, the N-intein is linked to the C-terminus of the N-terminal portion of the transcriptional activator or repressor and the test polypeptide is fused to the C-terminus of the N-intein. Optionally, a second expression vector is included in the kit. The second expression vector contains an expression cassette, which includes a first DNA sequence encoding a C-terminal portion of the transcriptional activator or repressor. The first DNA sequence is operably linked to a second DNA sequence encoding a C-intein. In addition, the expression vector comprises a restriction enzyme recognition site, preferably multiple cloning site (MCS) operably linked to the second DNA sequence encoding the C-intein such that a DNA fragment encoding a second test polypeptide of interest can be conveniently inserted in frame into the MCS and a fusion protein can be produced containing the C-intein, the C-terminal portion of the transcriptional activator or repressor and the second test polypeptide. Preferably, in the fusion protein, the C-intein is linked to the N-terminus of the C-terminal portion of the transcriptional activator or repressor and the test polypeptide is fused to the N-terminus of the C-intein. As a result, upon intein-mediated protein splicing, the N-terminal and C-terminal portion of the transcriptional activator or repressor can ligate and combine into a functional transcriptional activator or repressor. Preferably, the kit further includes a test yeast haploid precursor cell of the present invention.

The present invention will be further described by way of the following examples, which are not intended to limit the invention in any manner. Standard techniques well known in the art or the techniques specifically described below were utilized.

EXAMPLE

A yeast strain is constructed that contains: MATalpha1 null allele and MATalpha2 coding sequence under control of the GAL1 promoter in place of MATalpha locus; a LEU2-marked plasmid that expresses a fusion protein consisting of the GAL4 binding domain and the cytoplasmic domain of the R1 activin receptor; a TRP1-marked plasmid expressing a fusion of the GAL4 activation domain and FKBP12; deletion alleles of GAL4 and GAL80; and auxotrophic markers trp1, leu2, and his1. The haploid cells, which will be sterile due to R1-FKBP12 association, is mixed with an excess of cells of a MAT-alpha strain that carries the auxotrophic marker his4 and plated on agar medium lacking histidine. A previously identified inhibitor of R1-FKBP12 two-hybrid interactions, FK506, is spotted on the plate. FK506-induced dissociation of the R1-FKBP12 complex will convert the his1 cells to MATa-type phenotype, enabling the cells to mate with the bystander MATalpha his4 cells. Complementation of the his1 and his4 alleles will allow the resulting diploids to grow on the histidine-deficient medium, in contrast to either parental strain. Thus, compound-induced disruption of the protein-protein interaction is detected based on growth of diploid cells. Notably, once a test haploid cell has mated with a reporter haploid cell, the result is irreversible. That is, subsequent reassociation of the protein-protein interaction is without effect on the growth of the diploid. The effect of the compound need only be sufficiently prolonged to allow mating; once mating has occurred, the compound's effect is fixed and can be genetically selected.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for determining whether a first test polypeptide interacts with a second test polypeptide in the presence or absence of one or more test compounds, comprising:
   providing a test yeast haploid cell recombinantly expressing a first fusion protein and a second fusion protein, said first fusion protein containing said first test polypeptide and said second fusion protein containing said second test polypeptide, wherein said test yeast haploid cell is either sterile or capable of mating depending upon the presence or absence of a protein-protein interaction between said first test polypeptide and said second test polypeptide; and
   determining whether said test yeast haploid cell is capable of mating to form a yeast diploid cell in the presence or absence of one or more test compounds, thereby detecting the presence or absence of protein-protein interaction between said first test polypeptide and said second test polypeptide in the presence or absence of said one or more test compounds.

2. The method of claim 1, wherein said step of determining whether said test yeast haploid cell is capable of mating comprises co-culturing said test yeast haploid cell with a reporter yeast haploid cell of a- or alpha-mating type and selecting yeast diploid cells.

3. The method of claim 1, wherein the production of at least one alpha-specific gene-encoded protein in said test yeast haploid cell is controlled by the interaction between said first test polypeptide and said second test polypeptide, whereby said test yeast haploid cell either is sterile or exhibits alpha-mating type depending upon the presence or absence of a protein-protein interaction between said first and second test polypeptides.

4. The method of claim 1, wherein the production of at least one a-specific gene-encoded protein in said test yeast haploid cell is controlled by the interaction between said first test polypeptide and said second test polypeptide, whereby said test yeast haploid cell either is sterile or exhibits a-mating type depending upon the presence or absence of a protein-protein interaction between said first and second test polypeptides.

5. The method of claim 1, wherein the production of functional MAT-alpha1p and/or MAT-alpha2p in said test yeast haploid cell is controlled by the interaction between said first test polypeptide and said second test polypeptide.

6. The method of claim 1, wherein the test yeast haploid cell contains a reporter gene encoding MAT-alpha1p or MAT-alpha2p whose transcription is controlled by the interaction between said first test polypeptide and said second test polypeptide.

7. The method of claim 1, wherein said first fusion protein comprises a first effector polypeptide and said second fusion protein comprises a second effector polypeptide, and wherein said first and second effector polypeptides regulate the production of MAT-alpha1p and/or MAT-alpha2p.

8. The method of claim 7, wherein one of said first and second effector polypeptides is a DNA binding domain and the other is a transcriptional activation domain or transcriptional repressor domain, and wherein said test yeast haploid cell contains a reporter gene encoding MAT-alpha1p or MAT-alpha2p, the transcription of said reporter gene being controlled by the interaction between said first test polypeptide and said second test polypeptide, said interaction resulting in the reconstitution of a transcriptional activator from said DNA binding domain and said transcriptional activation domain or a transcriptional repressor from said DNA binding domain and said transcriptional repressor domain.

9. The method of claim 7, wherein one of said first and second effector polypeptides is a DNA binding domain and the other is a transcriptional activation domain or transcriptional repressor domain, and wherein said yeast haploid cell contains a relay gene encoding a transcriptional activator or repressor capable of activating or suppressing the expression of a reporter gene encoding MAT-alpha1p or MAT-alpha2p, the transcription of said relay gene being controlled by the interaction between said first test polypeptide and said second test polypeptide, said interaction resulting in the reconstitution of a transcriptional activator from said DNA binding domain and said transcriptional activation domain or a transcriptional repressor from said DNA binding domain and said transcriptional repressor domain.

10. The method of claim 7, wherein said first fusion protein comprises an N-terminal subdomain of ubiquitin linked to one of said first and second test polypeptides, said second fusion protein comprises a C-terminal subdomain of ubiquitin linked to the other of said first and second test polypeptides.

11. The method of claim 7, wherein said first fusion protein comprises an N-intein and said second fusion protein comprises a C-intein.

12. A method for detecting a protein-protein interaction between a first test polypeptide and a second test polypeptide, comprising:

providing a test yeast haploid cell expressing a first fusion protein containing said first test polypeptide and a second fusion protein containing said second test polypeptide, wherein said test yeast haploid cell exhibits one of the a- and alpha-mating types when said first test polypeptide interacts with said second test polypeptide, and wherein said test yeast haploid cell is sterile in the absence of an interaction between said first and second test polypeptides; and co-culturing said test yeast haploid cell and a reporter yeast haploid cell of the other of the a- and alpha-mating types opposite to that of said test yeast haploid cell under conditions conducive to mating, wherein the occurrence of mating between said test yeast haploid cell and said reporter yeast haploid cell is indicative of a protein-protein interaction between said first and second test polypeptides.

13. The method of claim 12, wherein said test yeast haploid cell lacks a functional MAT-alpha1p, wherein said test yeast haploid cell produces a functional MAT-alpha2p in the absence of an interaction between said first test polypeptide and said second test polypeptide, and wherein said test yeast haploid cell lacks a functional MAT-alpha2p in the presence of an interaction between said first test polypeptide and said second test polypeptide.

14. The method of claim 13, wherein the first fusion protein contains said first test polypeptide and a DNA binding domain, and said second fusion protein contains said second test polypeptide covalently linked to a transcriptional activation domain or transcriptional repressor domain.

15. The method of claim 13, wherein the first fusion protein contains said first test polypeptide and a DNA binding domain, and said second fusion protein contains said second test polypeptide covalently linked to a transcriptional repressor domain, wherein said test yeast haploid cell further contains a reporter gene encoding MAT-alpha2p and comprising an operator capable of binding to said DNA binding domain, and wherein in the absence of the interaction between said first and second test polypeptides said reporter gene is expressed and said test yeast haploid cell is sterile, while in the presence of the interaction between said first and second test polypeptides, said reporter gene is suppressed and said test yeast haploid cell exhibits a-mating type.

16. The method of claim 13, wherein said first fusion protein contains said first test polypeptide and a DNA binding domain, said second fusion protein contains said second test polypeptide and a transcriptional activation domain, wherein said test yeast haploid cell has a relay gene encoding a transcriptional repressor and having a promoter capable of binding to said DNA binding domain, wherein said test yeast haploid cell further contains a reporter gene encoding MAT-alpha2p and comprising an operator specific to said transcriptional repressor, and wherein said reporter gene is expressed and said test yeast haploid cell is sterile in the absence of the interaction between said first and second test polypeptides, while said reporter gene is suppressed and said test yeast haploid cell exhibits a-mating type in the presence of the interaction between said first and second test polypeptides.

17. The method of claim 13, wherein said first fusion protein comprises an N-terminal subdomain of ubiquitin, and said second fusion protein comprises a C-terminal subdomain of ubiquitin.

18. The method of claim 13, wherein said first fusion protein comprises an N-terminal subdomain of ubiquitin linked to said first test polypeptide, and second fusion protein comprises a C-terminal subdomain of ubiquitin linked at its N-terminus to said second test polypeptide and at its C-terminus to a transcriptional repressor;

wherein said test yeast haploid cell further comprises a reporter gene encoding MAT-alpha2p and having a promoter capable of binding to said transcriptional repressor;

wherein when said first test polypeptide interacts with said second test polypeptide, said N-terminal subdomain of ubiquitin and said C-terminal subdomain of ubiquitin associate with each other releasing a free form of said transcriptional repressor, which represses the expression of said reporter gene and cause the test yeast haploid cell to exhibit a-mating type; and wherein said reporter gene is expressed and said test yeast haploid cell is sterile in the absence of an interaction between said first and second test polypeptides.

19. The method of claim 13, wherein said first fusion protein contains an N-intein, and wherein said second fusion protein comprises a C-intein.

20. The method of claim 13, wherein said first fusion protein contains an N-terminal portion of MAT-alpha2p fused to the N-terminus of an N-intein and said first test polypeptide fused to the C-terminus of said N-intein, wherein said second fusion protein comprises a C-intein fused to the C-terminus of said second test polypeptide and a C-terminal portion of MAT-alpha2p fused to the C-terminus of the C-intein, wherein in the presence of an interaction between said first and second test polypeptides, an intein-mediated protein splicing occurs leading to the ligation of said N-terminal and C-terminal portions of MAT-alpha2p and the formation of a functional MAT-alpha2p.

21. The method of claim 12, wherein said test yeast haploid cell expresses a functional MAT-alpha2p, wherein said test yeast haploid cell lacks a functional MAT-alpha1p in the absence of an interaction between said first test polypeptide and said second test polypeptide, and wherein said test yeast haploid cell produces a functional MAT-alpha1p in the presence of an interaction between said first test polypeptide and said second test polypeptide.

22. The method of claim 21, wherein the first fusion protein contains said first test polypeptide and a DNA binding domain, and said second fusion protein contains said second test polypeptide covalently linked to a transcriptional activation domain or transcriptional repressor domain.

23. The method of claim 21, wherein said first fusion protein contains said first test polypeptide and a DNA binding domain and said second fusion protein contains said second test polypeptide and a transcriptional activation domain, wherein said test yeast haploid cell further comprises a reporter gene encoding MAT-alpha1p and comprising an operator capable of binding to said DNA binding domain, wherein when said first test polypeptide interacts with said second test polypeptide, said reporter gene is expressed and said test yeast haploid cell exhibits alpha-mating type, and wherein in the absence of the interaction between said first and second test polypeptides, said test yeast haploid cell is sterile.

24. The method of claim 21, wherein said first fusion protein comprises an N-terminal subdomain of ubiquitin linked to said first test polypeptide, said second fusion protein comprises a C-terminal subdomain of ubiquitin linked at its N-terminus to said second test polypeptide.

25. The method of claim 21, wherein said first fusion protein comprises an N-intein and said second fusion protein comprises a C-intein.

26. A method for selecting a compound capable of interfering with an interaction between a first test polypeptide and a second test polypeptide, comprising:

providing a test yeast haploid cell expressing a first fusion protein containing said first test polypeptide and a second fusion protein containing said second test polypeptide, wherein said test yeast haploid cell is sterile in the presence of the interaction between said first and second test polypeptides, and wherein said test yeast haploid cell exhibits one of the a- and alpha-mating types when the protein-protein interaction between said first test polypeptide and said second test polypeptide is disrupted;

co-culturing said test yeast haploid cell and a reporter yeast haploid cell of the other of the a- and alpha-mating types opposite to that of said test yeast haploid cell in the presence of a compound and under conditions conducive to mating, wherein the occurrence of mating between said test yeast haploid cell and said reporter yeast haploid cell would indicate that said compound is capable of disrupting the protein-protein interaction between said first test polypeptide and said second test polypeptide.

27. The method of claim 26, wherein said test yeast haploid cell lacks a functional MAT-alpha1p, wherein said test yeast haploid cell produces a functional MAT-alpha2p in the presence of an interaction between said first test polypeptide and said second test polypeptide, and wherein said test yeast haploid cell lacks a functional MAT-alpha2p in the absence of an interaction between said first test polypeptide and said second test polypeptide.

28. The method of claim 27, wherein the first fusion protein contains said first test polypeptide and a DNA binding domain, and said second fusion protein contains said second test polypeptide covalently linked to a transcriptional activation domain or transcriptional repressor domain.

29. The method of claim 27, wherein
the first fusion protein contains said first test polypeptide and a DNA binding domain;
said second fusion protein contains said second test polypeptide and a transcriptional activation domain;
said test yeast haploid cell further contains a reporter gene encoding MAT-alpha2p and comprising an operator capable of binding to said DNA binding domain, whereby in the absence of the interaction between said first and second test polypeptides said reporter gene is expressed and said test yeast haploid cell is sterile, while in the presence of the interaction between said first and second test polypeptides, said reporter gene is suppressed and said test yeast haploid cell exhibits a-mating type.

30. The method of claim 27, wherein
the first fusion protein contains the first test polypeptide and a DNA binding domain;
the second fusion protein contains the second test polypeptide and a transcriptional repressor domain;
said test yeast haploid cell contains a relay gene encoding a transcriptional repressor, said relay gene comprising a promoter having an operator capable of binding to said DNA binding domain;
said test yeast haploid cell further contains a reporter gene encoding MAT-alpha2p, said reporter gene comprising an operator responsive to said transcriptional repressor, whereby in the presence of an interaction between said first and second test polypeptides, said reporter gene is expressed and said test yeast haploid cell is sterile, while in the absence of the interaction between said first and second test polypeptides, said reporter gene is suppressed and said test yeast haploid cell exhibits a-mating type.

31. The method of claim 27, wherein said first fusion protein comprises an N-terminal subdomain of ubiquitin, and said second fusion protein comprises a C-terminal subdomain of ubiquitin.

32. The method of claim 27, wherein said first fusion protein contains an N-intein, and wherein said second fusion protein comprises a C-intein.

33. The method of claim 27, wherein
the first fusion protein contains an N-terminal portion of MAT-alpha2p fused to the N-terminus of an N-intein and the first test polypeptide fused to the C-terminus of said N-intein;
the second fusion protein comprises a C-intein fused to the C-terminus of the second test polypeptide and a C-terminal portion of MAT-alpha2p fused to the C-terminus of the C-intein, whereby in the presence of an interaction between said first and second test polypeptides, the test yeast haploid cell is sterile, while in the absence of an interaction between said first and second test polypeptides, said test yeast haploid cell exhibits a-mating type.

34. The method of claim 27, wherein
the first fusion protein contains an N-terminal portion of a transcriptional activator fused to the N-terminus of an N-intein and the first test polypeptide fused to the C-terminus of said N-intein;
the second fusion protein comprises a C-intein fused to the C-terminus of the second test polypeptide and a C-terminal portion of said transcriptional activator fused to the C-terminus of the C-intein;
said test yeast haploid cell further contains a reporter gene encoding MAT-alpha2p, said reporter gene comprising an operator responsive to said transcriptional activator, whereby in the presence of an interaction between said first and second test polypeptides, said reporter gene is expressed and said test yeast haploid cell is sterile, while in the absence of the interaction between said first and second test polypeptides, said test yeast haploid cell lacks a functional MAT-alpha2p and exhibits a-mating type.

35. The method of claim 26, wherein said test yeast haploid cell expresses a functional MAT-alpha2p, wherein said test yeast haploid cell lacks a functional MAT-alpha1p in the presence of an interaction between said first test polypeptide and said second test polypeptide, and wherein said test yeast haploid cell produces a functional MAT-alpha1p in the absence of an interaction between said first test polypeptide and said second test polypeptide.

36. The method of claim 35, wherein the first fusion protein contains said first test polypeptide and a DNA binding domain, and said second fusion protein contains said second test polypeptide covalently linked to a transcriptional activation domain or transcriptional repressor domain.

37. The method of claim 35, wherein said first fusion protein contains said first test polypeptide and a DNA binding domain and said second fusion protein contains said second test polypeptide and a transcriptional repressor domain, wherein said test yeast haploid cell further comprises a reporter gene encoding MAT-alpha1p and comprising an operator capable of binding to said DNA binding domain, whereby when said first test polypeptide interacts with said second test polypeptide, said reporter gene is suppressed and said test yeast haploid cell is sterile, while in the absence of the interaction between said first and second test polypeptides, said test yeast haploid cell exhibits alpha-mating type.

38. The method of claim 35, wherein said first fusion protein comprises an N-terminal subdomain of ubiquitin linked to said first test polypeptide, said second fusion protein comprises a C-terminal subdomain of ubiquitin linked at its N-terminus to said second test polypeptide.

39. The method of claim 35, wherein said first fusion protein comprises an N-intein and said second fusion protein comprises a C-intein.

40. A yeast haploid cell comprising:
a first chimeric gene encoding a first fusion protein which contains a first test polypeptide and a first effector polypeptide; and
a second chimeric gene encoding a second fusion protein which contains a second test polypeptide and a second effector polypeptide, wherein said yeast haploid cell is either sterile or capable of mating depending upon the presence or absence of a protein-protein interaction between said first test polypeptide and said second test polypeptide.

41. The yeast haploid cell of claim 40, wherein the production of at least one alpha-specific gene-encoded protein or at least one a-specific gene-encoded protein in said test yeast haploid cell is dependent on the interaction between said first test polypeptide and said second test polypeptide, whereby said yeast haploid cell either is sterile or exhibits alpha-mating type or a-mating type depending upon the presence or absence of the protein-protein interaction between said first and second test polypeptides.

42. The yeast haploid cell of claim 40, wherein the production of functional MAT-alpha1p and/or MAT-alpha2p in said yeast haploid cell is controlled by the interaction between said first test polypeptide and said second test polypeptide.

43. The yeast haploid cell of claim 42, wherein said yeast haploid cell lacks a functional MAT-alpha1p, and wherein the production of a functional MAT-alpha2p in said yeast haploid cell is dependent on the interaction between said first test polypeptide and said second test polypeptide.

44. The yeast haploid cell of claim 42, wherein said yeast haploid cell expresses a functional MAT-alpha2p, and wherein the production of a functional MAT-alpha1p in said yeast haploid cell is dependent on the interaction between said first test polypeptide and said second test polypeptide.

45. The yeast haploid cell of claim 42, wherein the yeast haploid cell contains a reporter gene encoding MAT-alpha1p or MAT-alpha2p whose expression is controlled by the interaction between said first test polypeptide and said second test polypeptide.

46. The yeast haploid cell of claim 45, wherein one of said first and second effector polypeptides is a DNA binding domain and the other is a transcriptional activation domain or transcriptional repressor domain, and wherein the expression of said reporter gene is controlled by the interaction between said first test polypeptide and said second test polypeptide, said interaction leading to the reconstitution of a transcriptional activator from said DNA binding domain and said transcriptional activation domain or a transcriptional repressor from said DNA binding domain and said transcriptional repressor domain.

47. The yeast haploid cell of claim 45, wherein
one of said first and second effector polypeptides is a DNA binding domain and the other is a transcriptional activation domain or transcriptional repressor domain;
said yeast haploid cell contains a relay gene encoding a transcriptional activator or repressor capable of activating or suppressing the expression of said reporter gene, the expression of said relay gene being controlled by the interaction between said first test polypeptide and said second test polypeptide, said interaction causing the reconstitution of a transcriptional activator from said DNA binding domain and said transcriptional activation domain or a transcriptional repressor from said DNA binding domain and said transcriptional repressor domain.

48. The yeast haploid cell of claim 42, wherein said first fusion protein comprises an N-terminal subdomain of ubiquitin linked to said first test polypeptide, said second fusion protein comprises a C-terminal subdomain of ubiquitin linked at its N-terminus to said second test polypeptide and at its C-terminus to MAT-alpha1p or MAT-alpha2p, wherein said N-terminal subdomain of ubiquitin and said C-terminal subdomain of ubiquitin associate with each other releasing said MAT-alpha1p or MAT-alpha2p only when said first test polypeptide interacts with said second test polypeptide.

49. The yeast haploid cell of claim 42, wherein said first effector polypeptide is an N-intein, and wherein said second effector polypeptide is a C-intein.

50. A yeast haploid cell comprising:
a first chimeric gene encoding a first fusion protein which contains a first test polypeptide and a first effector polypeptide;
a second chimeric gene encoding a second fusion protein which contains a second test polypeptide and a second effector polypeptide, one of said first and second effector polypeptides being a DNA binding domain and the other being a transcriptional activation domain; and
a reporter gene encoding MAT-alpha2p comprising an operator capable of binding to said DNA binding domain, wherein said yeast haploid cell lacks a functional MAT-alpha1p, said reporter gene is expressed and said yeast haploid cell is sterile in the presence of an interaction between said first test polypeptide and said second test polypeptide, and wherein said reporter gene is not expressed and said yeast haploid cell exhibits the a-mating type when the protein-protein interaction between said first and second test polypeptides is disrupted.

51. A yeast haploid cell comprising:
a first chimeric gene encoding a first fusion protein which contains a first test polypeptide and a first effector polypeptide;
a second chimeric gene encoding a second fusion protein which contains a second test polypeptide and a second effector polypeptide, one of said first and second effector polypeptides being a DNA binding domain and the other being a transcriptional repressor domain; and
a reporter gene encoding MAT-alpha2p and comprising an operator capable of binding to said DNA binding domain, wherein said yeast haploid cell lacks a functional MAT-alpha1p, said reporter gene is expressed and said yeast haploid cell is sterile in the absence of interaction between said first and second test polypeptides, and wherein said reporter gene is suppressed and said yeast haploid cell exhibits a-mating type in the presence of interaction between said first and second test polypeptides.

52. A kit comprising in a compartmentalized carrier:
a first yeast haploid cell having a genotype of mat-alpha1−; and
a second yeast haploid cell which is a reporter yeast haploid cell of alpha-mating type,
wherein said first yeast haploid cell has a first reporting marker and said second yeast haploid cell has a second reporting marker that is different from said first reporting marker, and wherein said first yeast haploid cell comprises a reporter gene encoding a functional MAT-alpha2p and having a promoter responsive to a transcriptional activator or repressor not expressed by said first yeast haploid cell.

53. A kit comprising in a compartmentalized carrier:

a yeast haploid cell having the genotype of mat-alpha1$^-$;

a first expression vector containing a first expression cassette which comprises a first DNA sequence encoding a DNA binding domain operably linked to a first multiple cloning site (MCS);

a second expression vector containing a second expression cassette which comprises a second DNA sequence encoding a transcriptional activation domain or a transcriptional repressor domain, said second DNA sequence being operably linked to a second multiple cloning site (MCS).

54. The kit of claim 53, wherein said yeast haploid cell comprises a reporter gene encoding a functional MAT-alpha2p and having a promoter capable of binding said DNA binding domain.

55. A kit comprising in a compartmentalized carrier:

a first expression vector containing a first expression cassette which comprises, operably linked together, (1) a first DNA sequence encoding an N-intein, (2) a first multiple cloning site (MCS), and (3) a second DNA sequence encoding an N-terminal portion of a transcriptional activator or repressor;

a second expression vector containing a second expression cassette which comprises, operably linked together, (4) a third DNA sequence encoding a C-intein, (5) a second multiple cloning site (MCS), and (6) a C-terminal portion of said transcriptional activator or repressor; and a yeast haploid cell containing a reporter gene encoding a functional MAT-alpha2p or MAT-alpha1p, the expression of said reporter gene being controlled by said transcriptional activator or repressor.

56. A kit comprising in a compartmentalized carrier:

a first expression vector containing a first expression cassette which comprises, operably linked together, (1) a first DNA sequence encoding an N-intein, (2) a first multiple cloning site (MCS), and (3) a second DNA sequence encoding an N-terminal portion of MAT-alpha1p or MAT-alpha2p;

a second expression vector containing a second expression cassette which comprises, operably linked together, (4) a third DNA sequence encoding a C-intein, (5) a second multiple cloning site (MCS), and (6) a C-terminal portion of said MAT-alpha1p or MAT-alpha2p.

57. A kit for selecting a compound capable of interrupting a protein-protein interaction, comprising:

a first yeast cell which is a yeast haploid cell lacking a functional MAT-alpha1p and having a MAT-alpha2 gene whose expression is under the control of a heterogeneous promoter capable of binding to a DNA binding domain of a transcriptional activator, wherein said first yeast cell exhibits a-mating type in the absence of the expression of said MAT-alpha2 gene and wherein said yeast haploid cell is sterile in the presence of the expression of said MAT-alpha2 gene;

a first expression vector having a DNA sequence encoding said DNA-binding domain operably linked to a multiple cloning site;

a second expression vector having a DNA sequence encoding a transcriptional activation domain operably linked to another multiple cloning site; and a second yeast cell which is a reporter yeast haploid cell exhibiting alpha-mating type.

* * * * *

UNITED STATES PATENT AND TRADEMARK OFFICE
CERTIFICATE OF CORRECTION

PATENT NO. : 6,841,352 B2  Page 1 of 1
APPLICATION NO. : 10/186386
DATED : January 11, 2005
INVENTOR(S) : Kirill Ostanin It is certified that error appears in the above-identified patent and that said Letters Patent is hereby corrected as shown below:

Col. 38 Claim 18, line 16, please change "cause" to --causes--.

Col. 42 Claim 52, line 2-3, please change "mat-alpha1" to an italicized --*mat-alpha1*--.

Col. 43 Claim 53, line 2, please change "mat-alpha1" to an italicized --*mat-alpha1*--.

Signed and Sealed this

Twenty-eighth Day of April, 2009

JOHN DOLL
*Acting Director of the United States Patent and Trademark Office*